(12) United States Patent
Steege et al.

(10) Patent No.: US 8,915,940 B2
(45) Date of Patent: Dec. 23, 2014

(54) SURGICAL TOOL

(75) Inventors: Adam T. C. Steege, Chapel Hill, NC (US); Kyle W. Cobb, Brick, NJ (US); Ian M. McKinley, Venice, CA (US); Daniel M. Sievert, Seattle, WA (US)

(73) Assignee: Agile Endosurgery, Inc., Chapel Hill, NC (US)

( * ) Notice: Subject to any disclaimer, the term of this patent is extended or adjusted under 35 U.S.C. 154(b) by 557 days.

(21) Appl. No.: 13/014,248

(22) Filed: Jan. 26, 2011

(65) Prior Publication Data
US 2012/0143173 A1 Jun. 7, 2012

Related U.S. Application Data

(60) Provisional application No. 61/418,928, filed on Dec. 2, 2010.

(51) Int. Cl.
*A61B 19/00* (2006.01)
*A61B 17/29* (2006.01)

(52) U.S. Cl.
CPC .............. *A61B 19/2203* (2013.01); *A61B 17/29* (2013.01); *A61B 2017/291* (2013.01); *A61B 2017/2927* (2013.01); *A61B 2019/2215* (2013.01); *A61B 2019/2234* (2013.01); *A61B 2019/2242* (2013.01)
USPC ............................................. 606/205; 606/1

(58) Field of Classification Search
CPC ...................................................... A61B 19/22
USPC .............. 600/138–142, 146, 149; 606/1, 170, 606/205, 207, 208
See application file for complete search history.

(56) References Cited

U.S. PATENT DOCUMENTS 5,152,279 A 10/1992 Wilk
5,275,608 A 1/1994 Forman
(Continued)

FOREIGN PATENT DOCUMENTS

DE 3536747 A1 4/1986
DE 199409979 U1 11/1994
(Continued)

OTHER PUBLICATIONS

Thielman, S., et al., MICA—A new generation of versatile instruments in robotic surgery, The 2010 IEEE/RSJ International Conference on Intelligent Robots and Systems, pp. 871-878, Oct. 18-22, 2010, Taipei, Taiwan.
(Continued)

*Primary Examiner* — William Thomson
*Assistant Examiner* — John R Downey
(74) *Attorney, Agent, or Firm* — Michael G. Johnston; Moore & Van Allen PLLC

(57) ABSTRACT

A surgical tool for minimally invasive surgery. The surgical tool in one embodiment includes a manipulator as a user interface, a proximal universal joint mounted to the manipulator, a hollow elongated member such as a tube mounted to the proximal universal joint, and a distal universal joint mounted to the other end of the elongated member. An end effector is mounted to the distal universal joint second end. Pivoting of the first end of the proximal universal joint causes the second end of the distal universal joint to move in a corresponding motion, and cabling operatively couples the proximal and distal universal joints. The proximal and distal universal joints may each include two yokes and a center block. Cabling may include four cables that each engage two round elements at the proximal and distal universal joints mounting locations to the center block.

20 Claims, 34 Drawing Sheets

(56) References Cited

U.S. PATENT DOCUMENTS

| | | | |
|---|---|---|---|
| 5,405,344 A | 4/1995 | Williamson | |
| 5,441,494 A * | 8/1995 | Ortiz | 606/1 |
| 5,456,695 A | 10/1995 | Herve Dallemagne | |
| 5,549,636 A | 8/1996 | Li | |
| 5,620,415 A | 4/1997 | Lucey | |
| 5,643,294 A | 7/1997 | Tovey | |
| 5,647,526 A * | 7/1997 | Green et al. | 227/175.2 |
| 5,710,870 A | 1/1998 | Ohm | |
| 5,713,919 A * | 2/1998 | Lahr | 606/207 |
| 5,716,352 A | 2/1998 | Viola | |
| 5,752,973 A | 5/1998 | Kieturakis | |
| 5,785,647 A | 7/1998 | Tompkins | |
| 5,797,900 A | 8/1998 | Madhani | |
| 5,797,959 A | 8/1998 | Castro | |
| 5,825,982 A | 10/1998 | Wright | |
| 5,827,323 A * | 10/1998 | Klieman et al. | 606/205 |
| 5,836,960 A | 11/1998 | Kolesa | |
| 5,860,995 A | 1/1999 | Berkelaar | |
| 5,868,785 A | 2/1999 | Tal | |
| 5,898,599 A | 4/1999 | Massie | |
| 5,954,731 A | 9/1999 | Yoon | |
| 5,976,121 A | 11/1999 | Matern | |
| 5,993,410 A | 11/1999 | Vincent | |
| 6,197,017 B1 | 3/2001 | Brock | |
| 6,206,903 B1 | 3/2001 | Ramans | |
| 6,247,738 B1 | 6/2001 | Winkel | |
| 6,280,417 B1 | 8/2001 | Bohannon | |
| 6,299,625 B1 | 10/2001 | Bacher | |
| 6,364,888 B1 | 4/2002 | Niemeyer | |
| 6,371,952 B1 | 4/2002 | Madhani | |
| 6,385,509 B2 | 5/2002 | Das | |
| 6,394,998 B1 | 5/2002 | Wallace | |
| 6,443,944 B1 | 9/2002 | Doshi | |
| 6,592,572 B1 | 7/2003 | Suzuta | |
| 6,605,105 B1 | 8/2003 | Cuschieri | |
| RE38,335 E | 11/2003 | Aust | |
| 6,666,854 B1 | 12/2003 | Lange | |
| 6,673,092 B1 | 1/2004 | Bacher | |
| 6,685,698 B2 | 2/2004 | Morley | |
| 6,746,443 B1 * | 6/2004 | Morley et al. | 606/1 |
| 6,764,445 B2 | 7/2004 | Ramans | |
| 6,817,972 B2 | 11/2004 | Snow | |
| 6,817,974 B2 | 11/2004 | Cooper | |
| 6,913,613 B2 | 7/2005 | Schwarz | |
| 6,991,627 B2 | 1/2006 | Madhani | |
| 7,004,951 B2 | 2/2006 | Gibbens, III | |
| 7,083,616 B2 | 8/2006 | Kawai | |
| 7,101,363 B2 | 9/2006 | Nishizawa | |
| 7,121,781 B2 | 10/2006 | Sanchez | |
| 7,147,650 B2 * | 12/2006 | Lee | 606/205 |
| 7,204,168 B2 | 4/2007 | Najafi | |
| 7,241,288 B2 | 7/2007 | Braun | |
| 7,248,944 B2 | 7/2007 | Green | |
| 7,250,028 B2 | 7/2007 | Julian | |
| 7,338,513 B2 | 3/2008 | Lee | |
| 7,410,483 B2 * | 8/2008 | Danitz et al. | 606/1 |
| 7,494,499 B2 | 2/2009 | Nagase | |
| 7,507,232 B1 | 3/2009 | Garito | |
| 7,568,603 B2 | 8/2009 | Shelton, IV | |
| 7,588,175 B2 | 9/2009 | Timm et al. | |
| 7,674,255 B2 | 3/2010 | Braun | |
| 7,678,117 B2 * | 3/2010 | Hinman et al. | 606/108 |
| 7,686,819 B2 | 3/2010 | Kortenbach | |
| 7,736,356 B2 | 6/2010 | Cooper | |
| 7,819,884 B2 | 10/2010 | Lee | |
| 7,819,894 B2 | 10/2010 | Mitsuishi | |
| 7,824,401 B2 | 11/2010 | Manzo | |
| 7,828,808 B2 * | 11/2010 | Hinman et al. | 606/108 |
| 8,182,417 B2 * | 5/2012 | Danitz | 600/141 |
| 8,323,297 B2 * | 12/2012 | Hinman et al. | 606/108 |
| 2003/0236549 A1 | 12/2003 | Bonadio | |
| 2004/0030335 A1 | 2/2004 | Zenati | |
| 2004/0225323 A1 | 11/2004 | Nagase | |
| 2004/0236316 A1 * | 11/2004 | Danitz et al. | 606/1 |
| 2005/0015113 A1 | 1/2005 | Baptiste | |
| 2005/0096694 A1 | 5/2005 | Lee | |
| 2005/0143774 A1 | 6/2005 | Polo | |
| 2005/0240178 A1 | 10/2005 | Morley | |
| 2005/0251112 A1 * | 11/2005 | Danitz et al. | 606/1 |
| 2005/0273084 A1 | 12/2005 | Hinman et al. | |
| 2006/0094931 A1 * | 5/2006 | Danitz et al. | 600/141 |
| 2006/0095074 A1 | 5/2006 | Lee et al. | |
| 2006/0190034 A1 | 8/2006 | Nishizawa | |
| 2006/0206101 A1 * | 9/2006 | Lee | 606/1 |
| 2007/0151390 A1 | 7/2007 | Blumenkranz | |
| 2007/0179476 A1 * | 8/2007 | Shelton et al. | 606/1 |
| 2007/0208375 A1 | 9/2007 | Nishizawa | |
| 2007/0255289 A1 | 11/2007 | Nakao | |
| 2007/0287993 A1 * | 12/2007 | Hinman et al. | 606/1 |
| 2007/0288044 A1 | 12/2007 | Jinno | |
| 2008/0031243 A1 | 2/2008 | Hamed | |
| 2008/0065105 A1 | 3/2008 | Larkin | |
| 2008/0103452 A1 * | 5/2008 | Voegele et al. | 604/187 |
| 2008/0221590 A1 | 9/2008 | Ikeda | |
| 2008/0255421 A1 * | 10/2008 | Hegeman et al. | 600/139 |
| 2008/0262538 A1 * | 10/2008 | Danitz et al. | 606/205 |
| 2008/0287862 A1 | 11/2008 | Weitzner | |
| 2008/0308606 A1 * | 12/2008 | Timm et al. | 227/175.2 |
| 2008/0319474 A1 | 12/2008 | Kishi | |
| 2009/0012538 A1 | 1/2009 | Saliman | |
| 2009/0054733 A1 | 2/2009 | Marescaux | |
| 2009/0069842 A1 | 3/2009 | Lee | |
| 2009/0320637 A1 | 12/2009 | Doyle | |
| 2009/0326552 A1 | 12/2009 | Diolaiti | |
| 2010/0082039 A1 | 4/2010 | Mohr | |
| 2010/0087818 A1 | 4/2010 | Cunningham | |
| 2010/0160724 A1 | 6/2010 | Prisco | |
| 2010/0160929 A1 | 6/2010 | Rogers | |
| 2010/0168744 A1 | 7/2010 | Sugiyama | |
| 2010/0179587 A1 | 7/2010 | Grant | |
| 2010/0249759 A1 * | 9/2010 | Hinman et al. | 606/1 |
| 2010/0262180 A1 | 10/2010 | Danitz et al. | |
| 2010/0305552 A1 * | 12/2010 | Shelton et al. | 606/1 |
| 2010/0331857 A1 | 12/2010 | Doyle et al. | |
| 2011/0022078 A1 | 1/2011 | Hinman | |
| 2011/0105843 A1 | 5/2011 | Mueller | |
| 2012/0095451 A1 * | 4/2012 | Hegeman et al. | 606/1 |
| 2013/0060239 A1 * | 3/2013 | Hinman et al. | 606/1 |

FOREIGN PATENT DOCUMENTS

| | | |
|---|---|---|
| DE | 19608809 A1 | 9/1997 |
| DE | 19647761 C1 | 1/1998 |
| DE | 19739002 A1 | 4/1998 |
| DE | 19702079 A1 | 7/1998 |
| DE | 19942738 A1 | 3/2000 |
| DE | 10012560 A1 | 9/2001 |
| DE | 10143753 A1 | 4/2003 |
| DE | 69918569 T2 | 3/2005 |
| DE | 69731521 T2 | 3/2006 |
| DE | 102004059235 B3 | 5/2006 |
| DE | 60022911 T2 | 6/2006 |
| DE | 102004061477 A1 | 6/2006 |
| DE | 102004054866 B3 | 8/2006 |
| DE | 102005054575 B3 | 4/2007 |
| DE | 60029234 T2 | 5/2007 |
| DE | 102006059379 A1 | 8/2007 |
| DE | 102006020013 A1 | 12/2007 |
| DE | 102006059952 B3 | 6/2008 |
| DE | 102007022122 A1 | 11/2008 |
| DE | 102008005901 A1 | 8/2009 |
| DE | 102008006982 A1 | 8/2009 |
| DE | 102008016708 A1 | 10/2009 |
| DE | 102008001664 A1 | 11/2009 |
| DE | 102008041260 A1 | 2/2010 |
| DE | 102008041602 A1 | 3/2010 |
| DE | 102008041709 A1 | 3/2010 |
| DE | 102008041867 A1 | 3/2010 |
| EP | 539195 A2 | 4/1993 |
| EP | 1066799 A2 | 1/2001 |
| EP | 1754448 A1 | 2/2007 |
| EP | 1813212 A1 | 8/2007 |
| EP | 1854418 A1 | 11/2007 |
| EP | 1886630 A2 | 2/2008 |

(56) References Cited

FOREIGN PATENT DOCUMENTS

| | | |
|---|---|---|
| EP | 1915950 A1 | 4/2008 |
| EP | 2058090 A2 | 5/2009 |
| EP | 2361578 A2 | 8/2011 |
| GB | 2421912 A | 7/2006 |
| JP | 6047052 A | 2/1994 |
| JP | 2009165504 A | 7/2009 |
| WO | WO 9219146 A1 | 11/1992 |
| WO | WO 9511630 A1 | 5/1994 |
| WO | WO 9720506 A1 | 6/1997 |
| WO | WO 9743942 A1 | 11/1997 |
| WO | WO 9819222 A1 | 5/1998 |
| WO | WO 0243569 A2 | 6/2002 |
| WO | WO 03001986 A2 | 1/2003 |
| WO | WO 03066288 A1 | 8/2003 |
| WO | WO 2005046500 A1 | 5/2005 |
| WO | WO 2005055840 A1 | 6/2005 |
| WO | 2006075153 A1 | 7/2006 |
| WO | WO 2006124390 A2 | 11/2006 |
| WO | WO 2007088208 A1 | 8/2007 |
| WO | WO 2007111571 A1 | 10/2007 |
| WO | WO 2009091497 A2 | 7/2009 |
| WO | WO 2009123891 A1 | 10/2009 |
| WO | WO 2009126955 A2 | 10/2009 |
| WO | WO 2009150184 A1 | 12/2009 |
| WO | WO 2010009221 A2 | 1/2010 |
| WO | WO 2010009224 A1 | 1/2010 |
| WO | WO 2010112608 A1 | 10/2010 |
| WO | WO 2010127109 A1 | 11/2010 |
| WO | WO 2010138083 A1 | 12/2010 |
| WO | WO 2011109640 A1 | 9/2011 |
| WO | WO 2012074564 A1 | 6/2012 |
| WO | WO 2012078951 A1 | 6/2012 |
| WO | WO 2013009699 A2 | 1/2013 |
| WO | WO 2013166409 A1 | 11/2013 |

OTHER PUBLICATIONS

Seibold, U., et al., Endoscopic 3 DoF-Instrument with 7 DoF Force/Torque Feedback, 4 pages.

Hagn, Ulrich, et al., DLR MiroSurge: a versatile system for research in endoscopic telesurgery, Int J CARS, 2010, pp. 183-193, vol. 5.

Hagn, Ulrich, et al., Telemanipulator for Remote Minimally Invasive Surgery: Requirements for a Light-Weight Robot for Both Open and Laparoscopic Surgery, IEEE Robotics & Automation Magazine, Dec. 2008, pp. 28-38.

Seibold, Ulrich, et al., Prototypic force feedback instrument for minimally invasive robotic surgery, Medical Robotics, pp. 377-400.

Kübler, B., et al., Prototypic Setup of a Surgical Force Feedback Instrument for Minimally Invasive Robotic Surgery, Abstractband: 12.-14., 2006.

Kuebler, B., et al., Development of actuated and sensor integrated forceps for minimally invasive robotic surgery, Int J Medical Robotics and Computer Assisted Surgery, 2005, pp. 96-107, vol. 1, No. 3.

Deml, Barbara, et al., The Touch and Feel in Minimally Invasive Surgery, HAVE 2005—IEEE International Workshop on Haptic Audio Visual Environments and their Applications, Ottawa, Ontario, Canada, Oct. 1-2, 2005, pp. 33-38.

Seibold, U., et al., Development of actuated and sensor integrated forceps for minimally invasive robotic surgery, 5th World Congress on Biomechanics, München.

Seibold, Ulrich, et al., Prototype of Instrument for Minimally Invasive Surgery with 6-Axis Force Sensing Capability, Proceedings of the 2005 IEEE International Conference on Robotics and Automation, Barcelona, Spain, Apr. 2005, pp. 496-501.

Seibold, Ulrich, et al., Sensorized and Actuate Instruments for Minimally Invasive Robotic Surgery, Proceedings of EuroHaptics, Munich Germany, Jun. 5-7, 2004, pp. 482-485.

Seibold, Ulrich, et al., a 6-Axis Force/Torque Sensor Design for Haptic Feedback in Minimally Invasive Robotic Surgery, In MICRO.tec—2nd VDE World Microtechnologies Congress, 2003, pp. 239-244.

Hamid, S.A., et al., Design and Synthesis of Wire-Actuated Universal-Joint Wrists for Surgical Applications, 2009 IEEE International Conference on Robotics and Automation, Kobe, Japan, May 12-17, 2009, pp. 1807-1813.

Universal Joint, Apr. 24, 2011, http://en.wikipedia.org/w/index.php?oldid=425662633.

Air Drone Robotics: VTOL UAV Delivery POD for Robotic Surgeon, AirStar International Inc. Home of the UAV Revolution, 2008.

Buntz, B., Surgical Instrument Incorporates Novel Universal Joint Design, Sep. 1, 2007, European Medical Devices Technology.

Belden, Inc., Small in size, big on precision—Miniature universal joints in minimally invasive surgical device, Press Release.

DLR Institute of Robotics and Mechatronics, MICA—Actuated and sensorized surgical instuments, 2010, German Aerospace Center.

DLR Institute of Robots and Mechatronics, Medical Robotics with light-weight systems, 2010, German Aerospace Center.

Moore, M., M.D., Da Vinci Robotic Surgery, http://www.drmarkmoore.com/davinci_robotic_surgery_index.html.

Parpet, D., Universal Joint Carries Power in Surgical Device, Motion Control Technology, http://nasatech.com/motion/applications/apps1_0408.html.

U.S. Appl. No. 13/992,463, filed Jun. 7, 2013.

Freehand Endoscopic Devices, Inc., International Application No. PCT/US2011/064086, International Search Report and Written Opinion, May 11, 2012.

Freehand Endoscopic Devices, Inc., International Application No. PCT/US2011/064086, International Preliminary Report on Patentability, Jun. 20, 2013.

Freehand Endoscopic Devices, Inc., International Application No. PCT/US2011/022246, International Search Report and Written Opinion, Nov. 24, 2011.

Freehand Endoscopic Devices, Inc., International Application No. PCT/US2011/022246, Written Opinion, Dec. 14, 2012.

Freehand Endoscopic Devices, Inc., International Application No. PCT/US2011/022246, International Preliminary Report on Patentability, Mar. 7, 2013.

Agile Endosurgery, Inc., International Application No. PCT/US2013/039501, International Search Report and Written Opinion, Aug. 2, 2013.

Agile Endosurgery, Inc., International Application No. PCT/US2012/045951, International Search Report and Written Opinion, Jan. 10, 2013.

Agile Endosurgery, Inc., International Application No. PCT/US2014/041722, International Search Report and Written Opinion, Oct. 24, 2014.

* cited by examiner

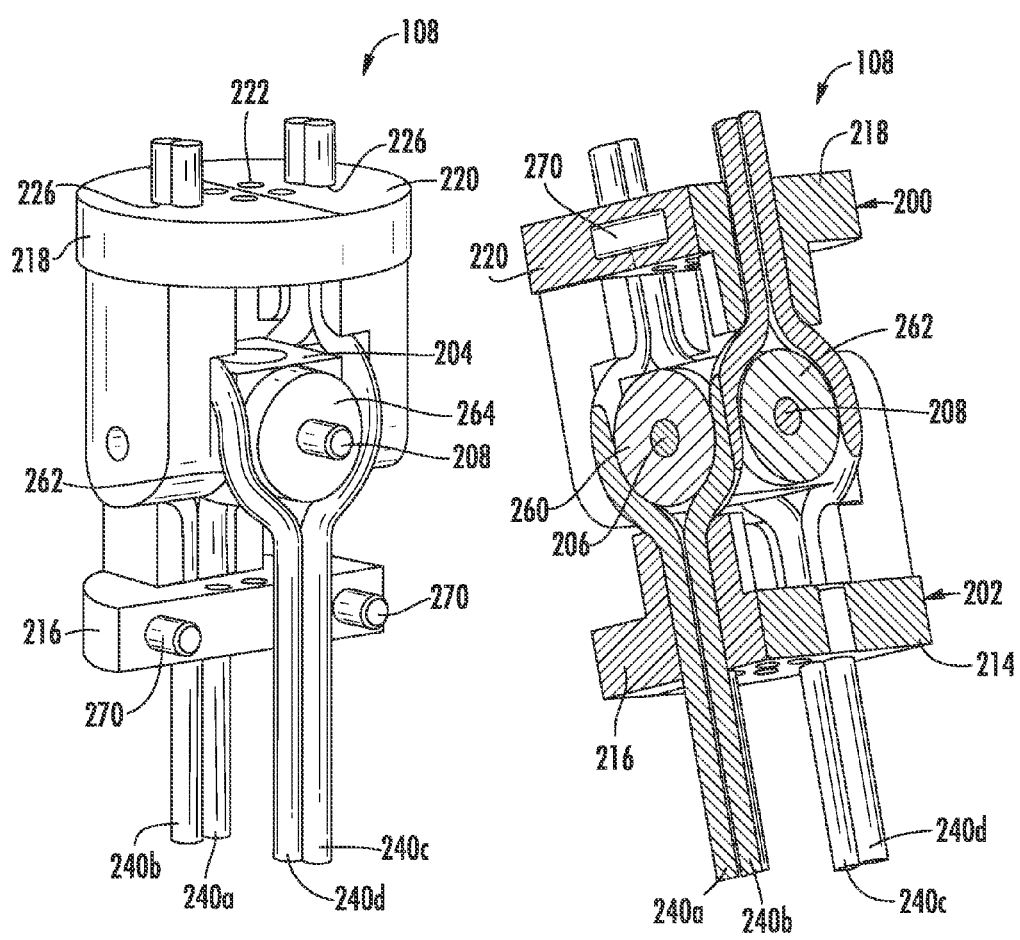

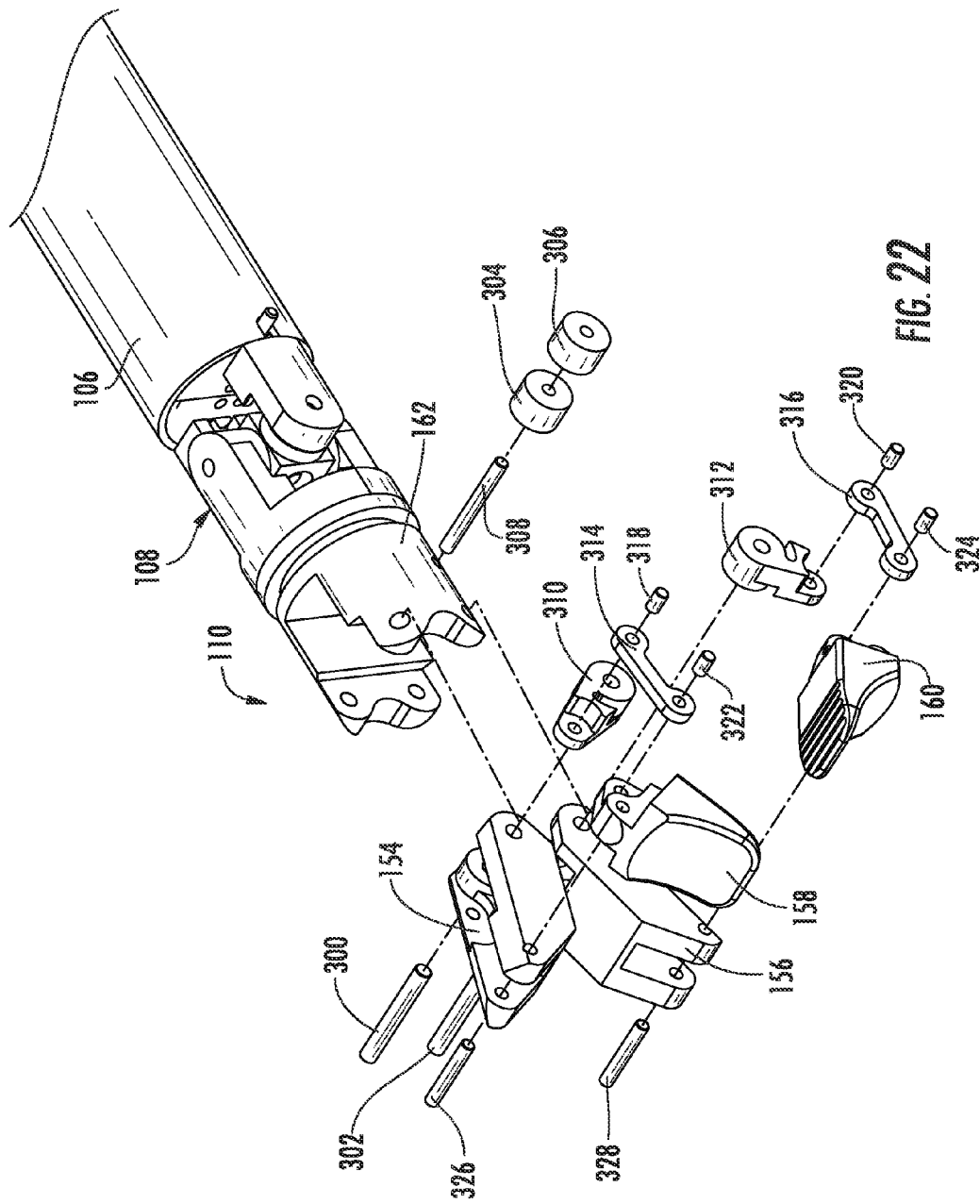

SURGICAL TOOL

CROSS REFERENCE TO RELATED APPLICATIONS

This application claims the benefit of U.S. Provisional Application No. 61/418,928, filed Dec. 2, 2010, entitled "SURGICAL TOOL," the contents of which are hereby incorporated by reference in their entirety.

BACKGROUND

Embodiments described herein generally relate to surgical apparatus for tissue and suture manipulation, and more particularly to apparatus that may be applied to conducting laparoscopic and endoscopic surgery.

Minimally invasive surgery, such as endoscopic surgery, encompasses a set of techniques and tools which are becoming more and more commonplace in the modern operating room. Minimally invasive surgery causes less trauma to the patient when compared to the equivalent invasive procedure. Hospitalization time, scarring, and pain are also decreased, while recovery rate is increased.

Endoscopic surgery is accomplished by the insertion of a cannula containing a trocar to allow passage of endoscopic tools. Optics for imaging the interior of the patient, as well as fiber optics for illumination and an array of grasping and cutting devices are inserted through a multiple cannulae, each with its own port.

Currently the majority of cutting and grasping tools are essentially the same in their basic structure. Standard devices consist of a user interface at the proximal end and an end effector at the distal end of the tool used to manipulate tissue and sutures. Connecting these two ends is a tube section, containing cables and/or rods used for transmitting motion from the user interface at the proximal end of the tool to the end effector at the distal end of the tool. The standard minimally invasive devices (MIDs) provide limited freedom of movement to the surgeon. The cannula has some flexibility of movement at the tissue wall, and the tool can rotate within the cannula, but tools cannot articulate within the patient's body, limiting their ability to reach around or behind organs or other large objects. Several manually operated devices have attempted to solve this problem with articulated surgical tools that are controlled much in the same way as standard MIDs. These devices have convoluted interfaces, making them more difficult to control than their robotic counterparts. Many lack torsional rigidity, limiting their ability to manipulate sutures and denser tissue.

Robotic surgical instruments have attempted to solve the problems that arise from the limitations of standard MIDs with telemetrically controlled articulated surgical tools. However, these tools are often prohibitively expensive to purchase and operate. The complexity of the devices raises the cost of purchasing as well as the cost of a service contract. These robotic solutions also have several other disadvantages such as complications during the suturing process. An additional and critical disadvantage is their lack of haptic feedback.

Due to variations in tissue density and structure, a surgeon will use many tools with differently shaped end effectors to manipulate tissue. This requires the surgeon to remove tools from their cannulae and replace them with different tools many times through the course of a procedure. Currently available MIDs do not provide the same versatility in tissue manipulation as is available in open surgery.

SUMMARY

In accordance with one embodiment, a surgical tool is provided for use by an operator. The surgical tool includes a manipulator adapted to receive at least a portion of the operator's hand. A proximal universal joint with a first end and a second end has its first end mounted to the manipulator, and a hollow elongated member has a first end that is mounted to the proximal universal joint second end, a second end, and a longitudinal axis. A distal universal joint has a first end that is mounted to the elongated member second end, and a second end. An end effector is mounted to the distal universal joint second end. In one embodiment, pivoting of the first end of the proximal universal joint causes the second end of the distal universal joint to move in a corresponding motion, and cabling operatively couples the proximal and distal universal joints.

In accordance with another embodiment, the proximal and distal universal joints each include a proximal yoke at the first end, a distal yoke at the second end, a center block, and means for pivoting the center member about two perpendicular, coplanar axes through the center block. The proximal yoke is mounted to the center block at first and second mounting locations, the distal yoke is mounted to the center block at third and fourth mounting locations, and between the center block and each yoke at each mounting location are round elements, which may be independent parts or integral to either of the center block or yokes. The cabling comprises four cables that each engage two of the round elements at each of the proximal and distal universal joints. Pivoting the proximal yoke on the proximal universal joint causes a corresponding motion of the distal yoke of the distal universal joint.

In accordance with another embodiment, an articulation system for a surgical tool is provided. The system includes a proximal universal joint including a proximal end member and a distal end member, a hollow elongated member having a first end, a second end, and a longitudinal axis, with the elongated member first end being mounted to the proximal universal joint distal end member, and a distal universal joint including a proximal end member and a distal end member, with the distal universal joint proximal end member being mounted to the elongated member second end. Universal joint control cables operatively connect the proximal and distal universal joints. Pivoting motion of the proximal end member of the proximal universal joint relative to the longitudinal axis of the elongated member exerts force on cables to cause a corresponding pivoting motion of the distal end member of the distal universal joint.

In accordance with another embodiment, a surgical tool for use by an operator is provided. The surgical tool includes a manipulator adapted to receive at least a portion of the operator's hand. The manipulator includes a mounting end, a first actuator, and a second actuator. A hollow elongated member has a first end, a second end, and a longitudinal axis, with the first end operatively connected to the mounting end of the manipulator. An end effector includes a mounting end that is operatively connected to the elongated member second end, and the end effector includes a base member and two opposed digits. Each digit includes a proximal phalange having a first end and a second end, with the first end pivotally mounted to the base member, and a distal phalange having a first end and a second, free end, with the first end pivotally mounted to the proximal phalange second end. The first actuator is operable to concurrently control the proximal phalanxes and the second actuator is operable to concurrently control the distal phalanxes.

In accordance with another embodiment, a method of operating a surgical tool is provided. The method includes pivoting the manipulator relative to the longitudinal axis of the elongated member to pivot the first end of the proximal universal joint, and pulling at least two cables with the pivoting of the proximal universal joint to cause the second end of the distal universal joint to pivot.

Further features of a surgical tool will become more readily apparent from the following detailed description taken in conjunction with accompanying drawings.

BRIEF DESCRIPTION OF THE DRAWINGS

For a more complete understanding, reference should now be had to the embodiments shown in the accompanying drawings and described below. In the drawings:

FIG. 20 is a perspective view of the distal universal joint assembly shown in FIG. 16 with a portion of a yoke removed.

FIG. 21 is a section view of the distal universal joint assembly shown in FIG. 16, taken along two faces of the distal universal joint assembly.

FIG. 22 is a partially exploded left perspective view of the end effector portion of the surgical tool shown in FIG. 1.

DETAILED DESCRIPTION

Figure 1:
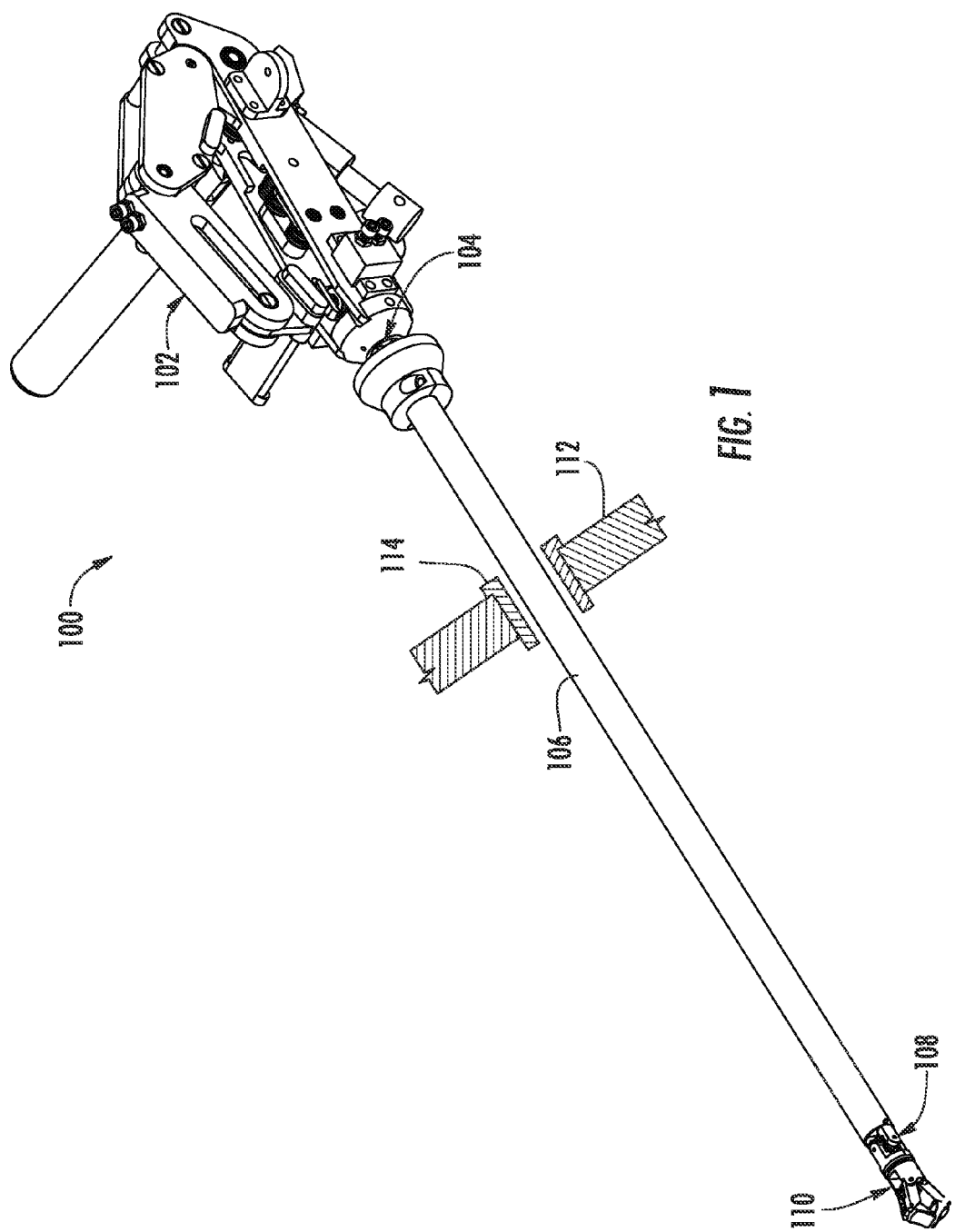
FIG. 1 is a perspective view of an embodiment of a surgical tool described herein.

Embodiments of a surgical instrument are disclosed for use in a wide variety of roles including, for example, grasping, dissecting, clamping, electrocauterizing, or retracting materials or tissue during surgical procedures performed within a patient's body.

Certain terminology is used herein for convenience only and is not to be taken as a limitation. For example, words such as "upper," "lower," "left," "right," "horizontal," "vertical," "upward," and "downward" merely describe the configuration shown in the figures. The components may be oriented in any direction and the terminology, therefore, should be understood as encompassing such variations unless specified otherwise.

Referring now to the drawings, wherein like reference numerals designate corresponding or similar elements throughout the several views, an embodiment of a surgical tool is shown in FIGS. 1-5 and is generally designated at 100. The surgical tool 100 includes embodiments of five primary components: a manipulator 102, a proximal universal joint 104, an elongated, hollow member or tube 106, a distal universal joint 108, and an end effector 110. The manipulator 102 attaches to the surgeon's hand, with fasteners such as hook and loop fastener straps (not shown) around the index finger and the thumb. The manipulator 102 and the end effector 110 and connected with cables, as discussed further below, such that when the surgeon moves his finger and thumb to control the manipulator 102, the end effector 110 has corresponding movements. The surgical tool 100 is shown in use in FIGS. 1 and 2, with a portion of the tube 106, the distal universal joint, and end effector 110 having passed through a tissue wall 112 via a cannula 114.

Figure 2:
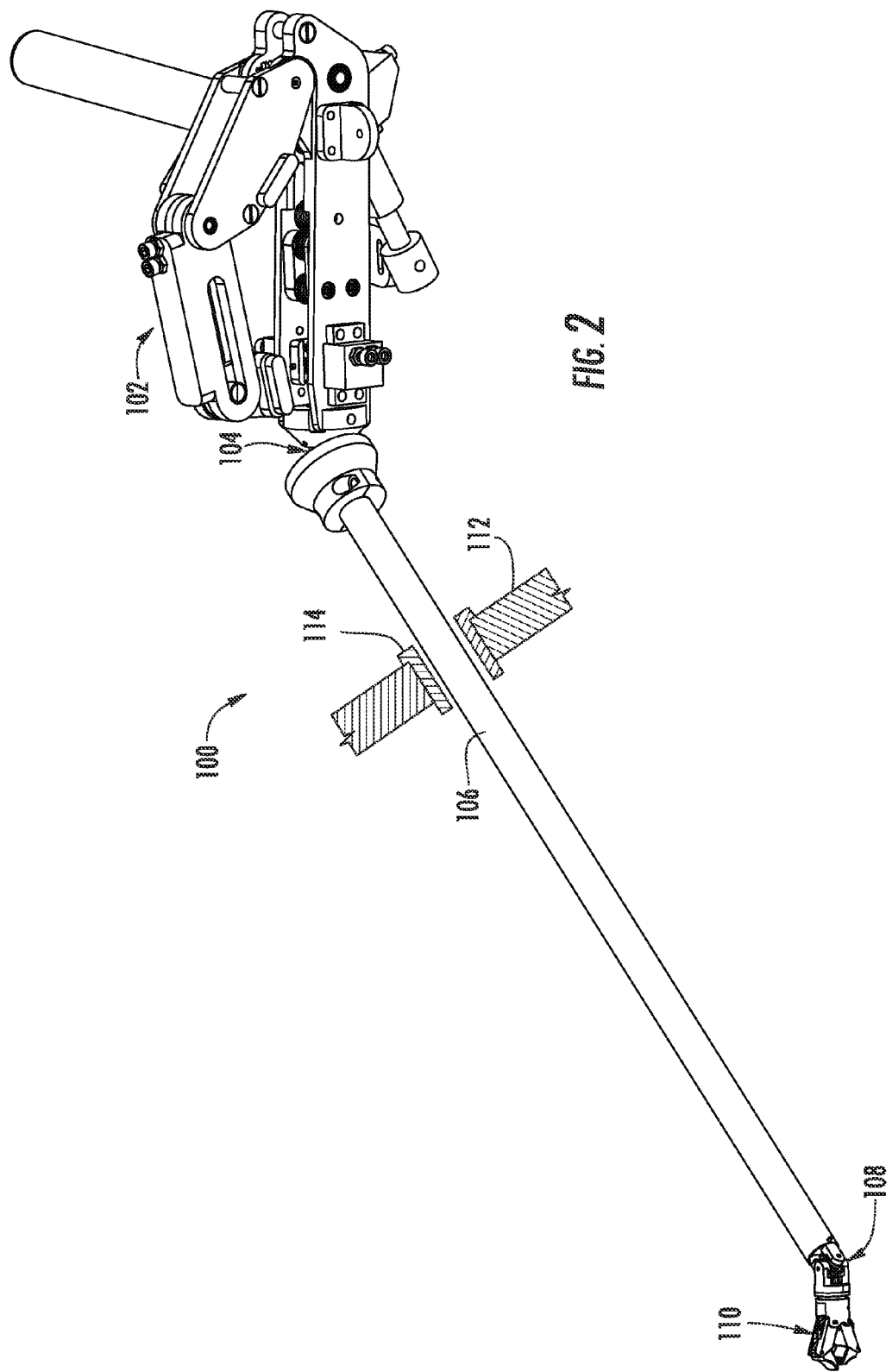
FIG. 2 is a perspective view of the surgical tool shown in FIG. 1 in an alternate position.
Figure 3:
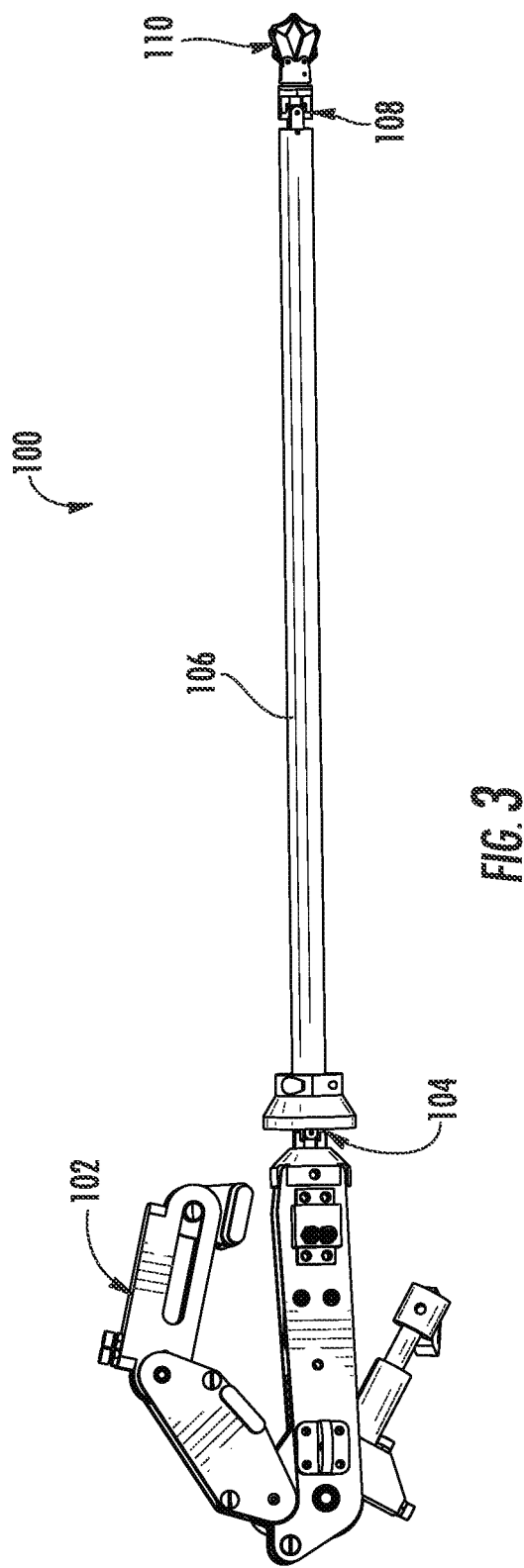
FIG. 3 is a left side view of the surgical tool shown in FIG. 1.
Figure 4:
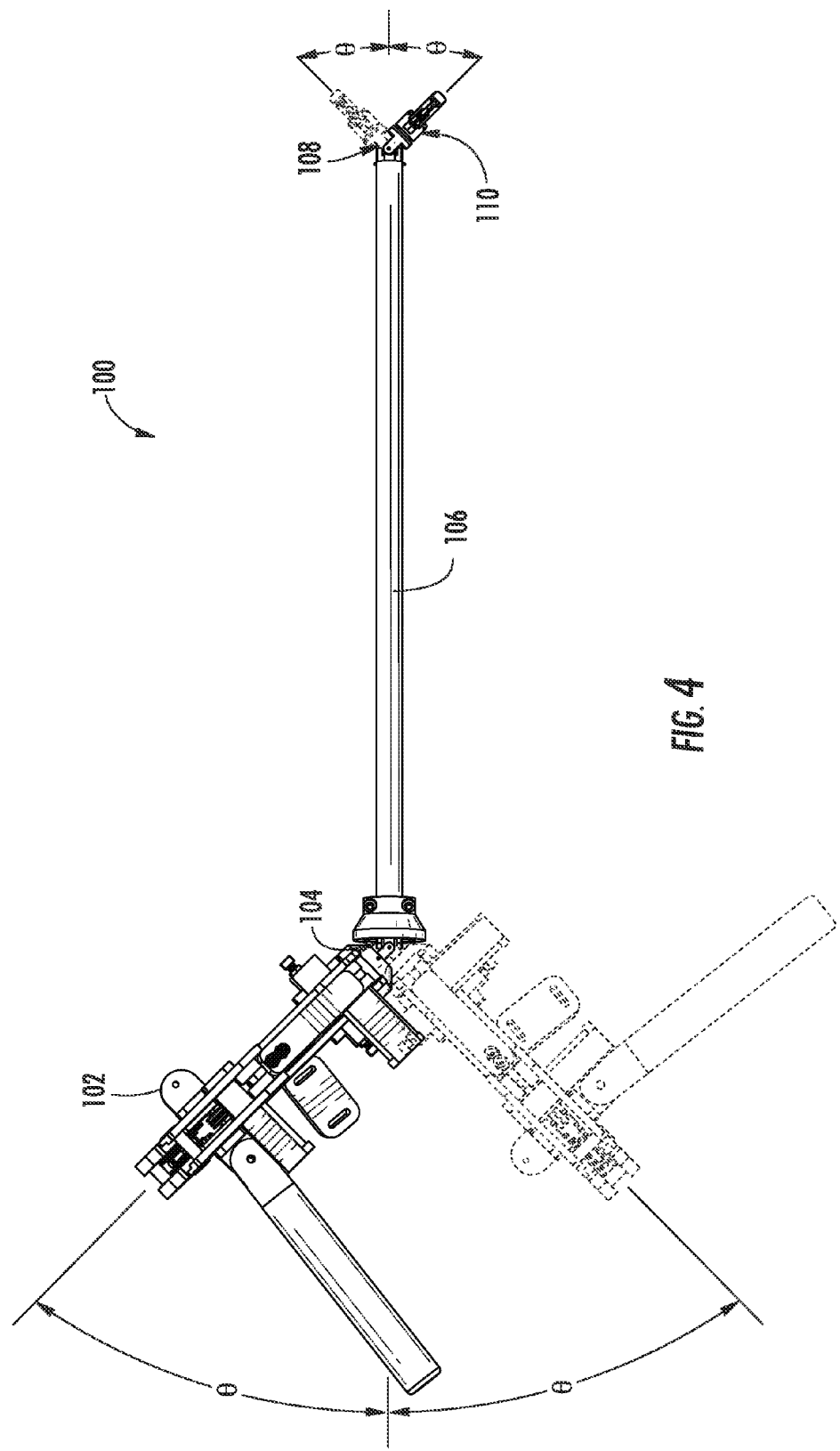
FIG. 4 is a top view of the surgical tool shown in FIG. 1.
Figure 5:
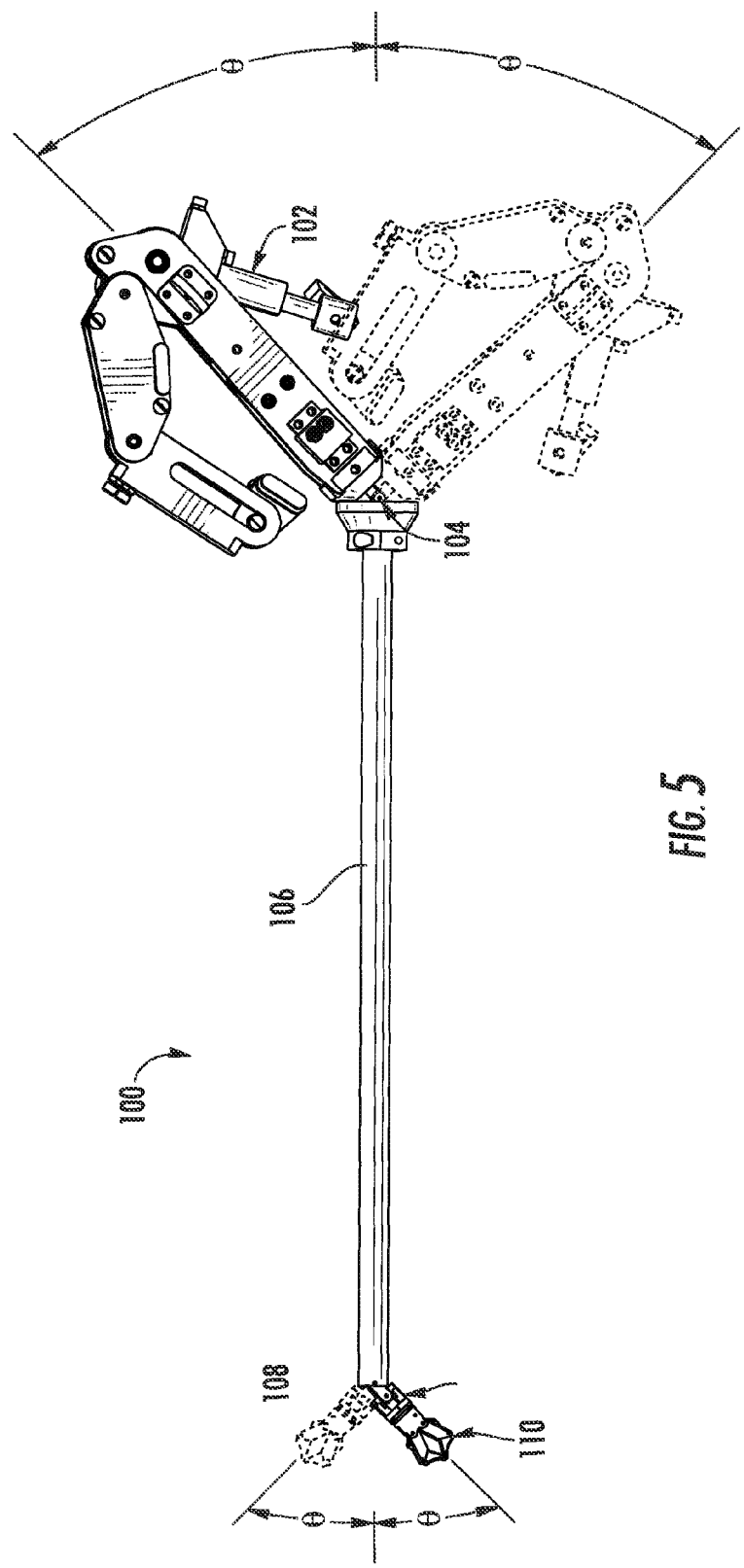
FIG. 5 is a right side view of the surgical tool shown in FIG. 1.

The movement of the proximal universal joint 104, which is attached to the manipulator 102, controls the movement of the distal universal joint 108. The universal joints 104, 108 are connected to each other with cables, as will be discussed further below, and each of the universal joints 104, 108 provide two degrees of freedom, being free to move in any combination of directions deflecting from the longitudinal axis of the tube 106. The cabling arrangement enables a surgeon to angle the manipulator 102 with his or her hand relative to the proximal universal joint 104 to cause the distal universal joint 108 to move in a similar manner in the opposite direction, imitating the surgeon's movements and providing directional control of the distal portion of the device. Such corresponding pivoted positions of the manipulator 102 and the end effector 110 relative to the longitudinal axis of the tube 106 are shown in FIGS. 2, 4, and 5. The maximum angle of deflection θ in every direction from the longitudinal axis of the tube 106 shows the range of motion at each end of the tool 100, and is determined by the design of the universal joints 104, 108 and the direction of deflection, and may vary from that shown. The tube 106 contains the cabling that connects the manipulator 102 to the end effector 110 and the proximal universal joint 104 to the distal universal joint 108.

FIGS. 6 through 13 depict the correlation between positions of the manipulator 102 and end effector 110. The manipulator 102 includes in the embodiment shown a base assembly 140, a thumb assembly 142, a primary index assembly 144, and a secondary index assembly 146. The manipulator 102 is shown in a right handed configuration, but the position of parts may be reversed to be for left handed use as well. The end effector 110 includes in the embodiment shown two digits 150, 152, each of which includes a proximal phalange 154, 156 and a distal phalange 158, 160 mounted to the respective proximal phalanxes 154, 156. The proximal phalanxes 154, 156 are mounted to a base member 162, which is mounted to the distal universal joint 108. The thumb assembly 142, primary index assembly 144, and secondary index assembly may be considered in this embodiment to be assemblies that are functionally levers, but the assemblies 142, 144, 146 may take other forms in different embodiments. The motion of the thumb assembly 142, which is followed by the primary index assembly 144, controls the motion of the both proximal phalanxes 154, 156 in the end effector 110. The motion of the secondary index assembly 146 controls the motion of both distal phalanxes 158, 160 in the end effector 110.

The end effector 110 may be designed to grasp, manipulate, and dissect tissue planes of varying densities and structures. The two digits 150, 152 of the embodiment of the end effector 110 of FIG. 7 move in a mirrored motion, such that the digits 150, 152 are symmetrical in angular position. The ability of the distal phalanxes 158, 160 of each digit 150, 152 to deflect inward while the proximal phalanxes 154, 156 of each digit 150, 152 are open allows the end effector 110 to pinch tissue, which may apply more pressure than in a standard tissue manipulating tool. Since the angle of deflection of the distal phalanxes 158, 160 is variable, the amount of potential pressure applied to tissue can be varied during operation depending on the density and structure of the tissue being manipulated. Additionally, the deflection of the distal phalanxes 158, 160 may permit the grasping and retraction of larger sections of tissue and organs than may be permitted by current tools. Alternatively, in some uses, for example, grasping sutures, it may be desirable to have an end effector that omits distal phalanxes, and accordingly would require a simpler manipulator. The surgical tool described herein may be adapted to accommodate a variety of types and designs of end effectors.

The user's hand is releasably attached to the manipulator 102 such that the tip of the index finger aligns with the adjustable finger grip 164 that is slidably mounted in a slot 166 in the secondary index assembly 146, and the tip of the thumb aligns with the adjustable thumb grip 168 on the thumb assembly 142. The index finger also attaches to a finger grip 170 on the primary index assembly 144 (portions of the grips 164, 170 where contact is made with the finger are not visible). These attachment points provide an interface for control of the manipulator 102 and corresponding actuation of the end effector 110.

Figure 6:
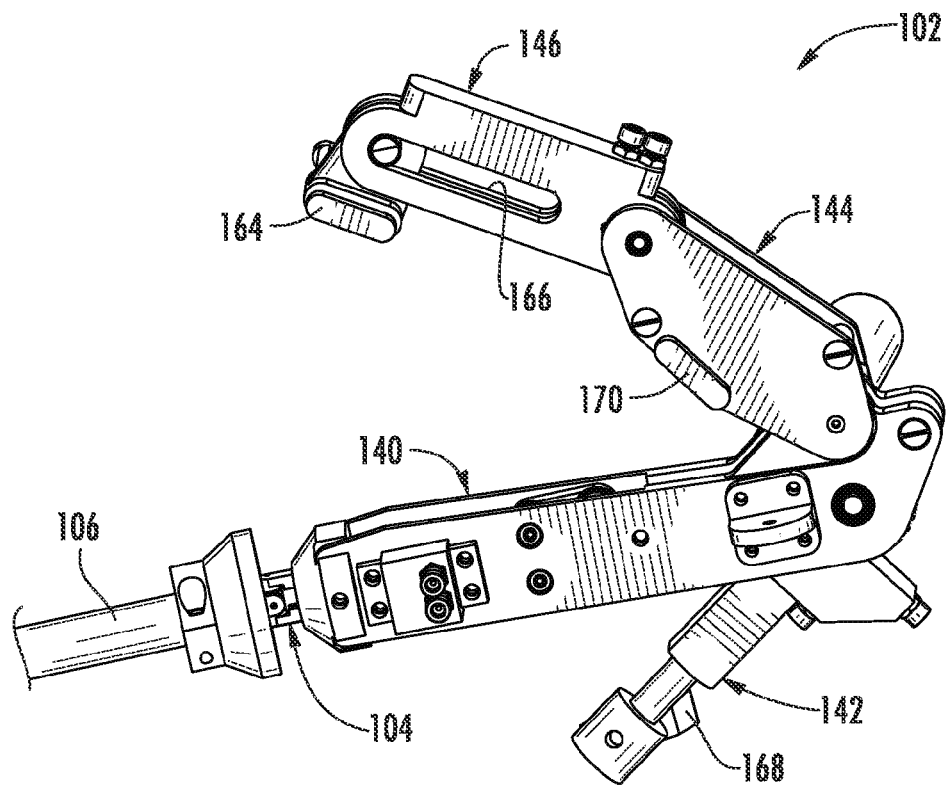
FIGS. 6 and 7 are left perspective views of a manipulator end portion and an end effector end portion, respectively, of the surgical tool shown in FIG. 1, in a corresponding first position.
Figure 7:
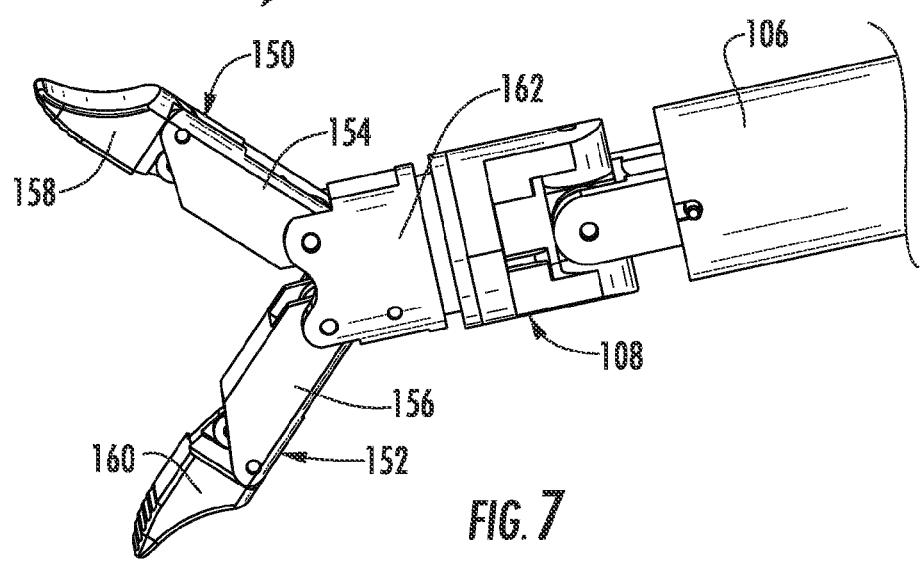

FIG. 6 shows the manipulator 102 in a position corresponding to the fully open position of the end effector 110 in FIG. 7. In FIG. 6, the primary index assembly 144 and thumb assembly 142 are deflected outward at the limit of their ranges of motion, and accordingly so are the proximal phalanxes 154, 156 in the end effector 110 in FIG. 7. Also shown in its fully outward deflected position, the secondary index assembly 146 of the manipulator 102 is only slightly offset from the angular position of the primary index assembly 144. In FIG. 7 and in the corresponding position, the distal phalanxes 158, 160 are substantially in alignment with the proximal phalanxes 154, 156. This positioning defines the fully open position.

Figure 8:
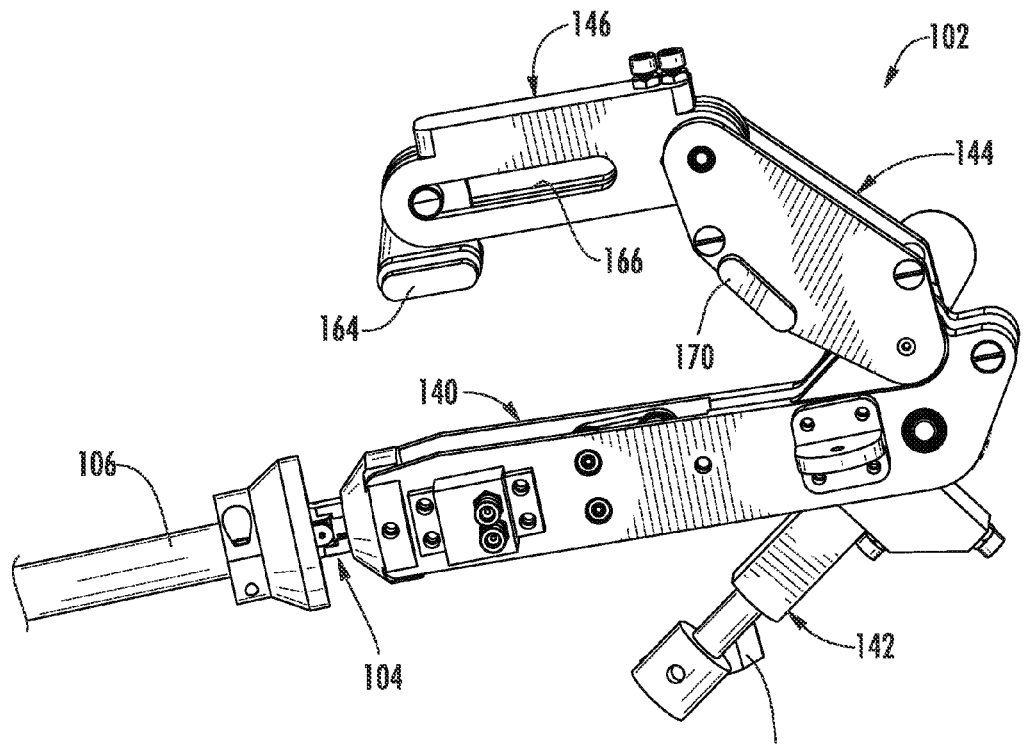
FIGS. 8 and 9 are left perspective views of the manipulator end portion and the end effector end portion, respectively, of the surgical tool shown in FIG. 1, in a corresponding second position.
Figure 9:
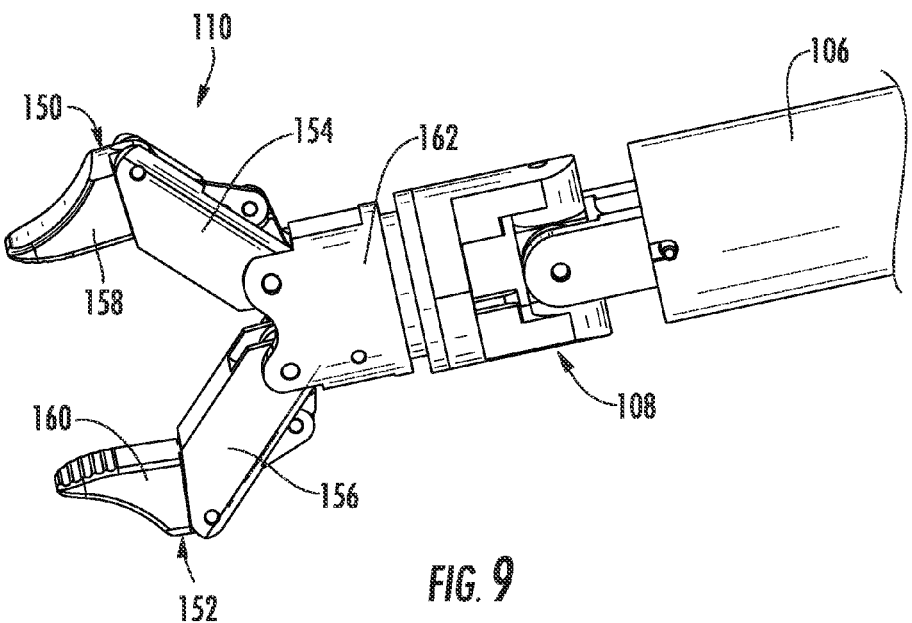

FIG. 8 shows the manipulator 102 in a position corresponding to the open gripping position of the end effector 110 in FIG. 9. In FIG. 8, the primary index assembly 144 and thumb assembly 142 are deflected outward at the limit of their ranges of motion as in FIG. 6, and accordingly so are the proximal phalanxes 154, 156 in the end effector 110 in FIG. 9. The secondary index assembly 146 of the manipulator 102 is deflected inward at the limit of its range of motion, and the distal phalanxes 158, 160 in the end effector 110 are in their corresponding inward position in FIG. 9.

Figure 10:
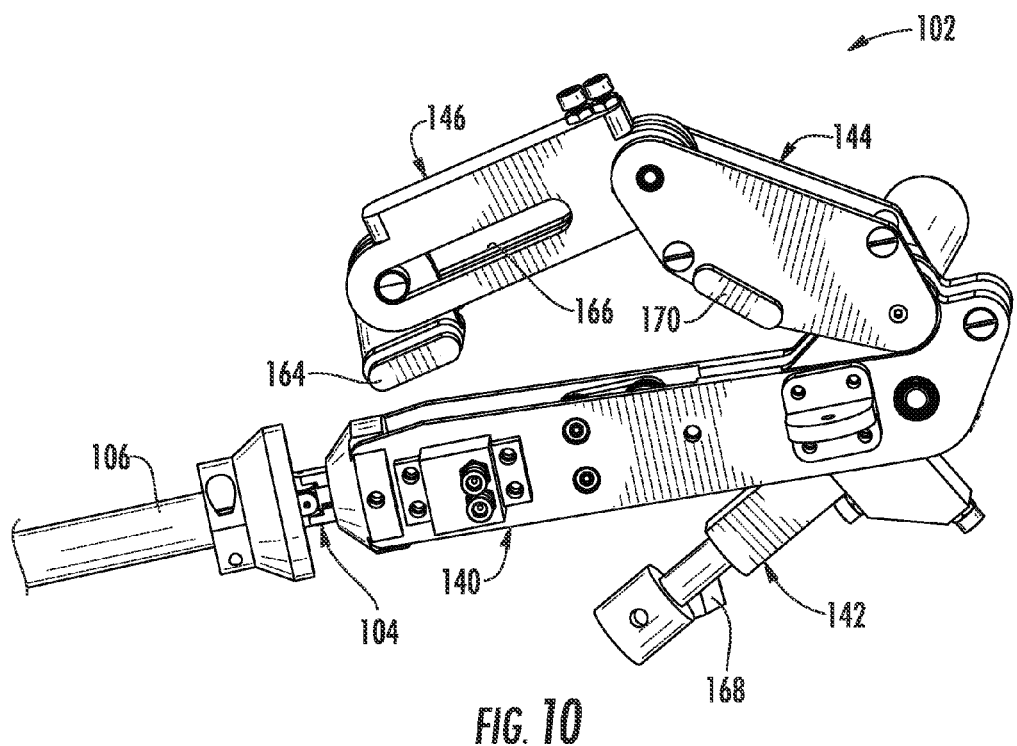
FIGS. 10 and 11 are left perspective views of the manipulator end portion and the end effector end portion, respectively, of the surgical tool shown in FIG. 1, in a corresponding third position.
Figure 11:
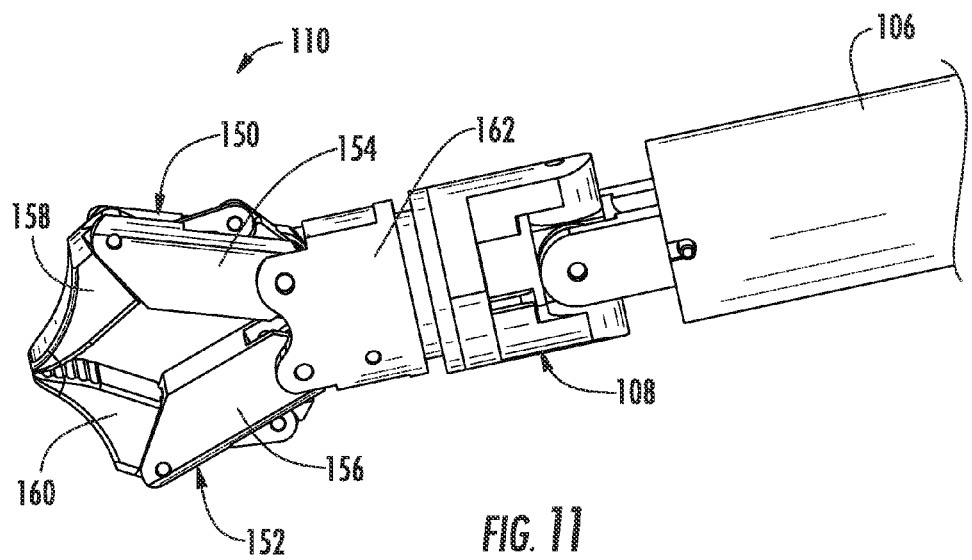

FIG. 10 shows the manipulator 102 in a position corresponding to the closed pinching position of the end effector 110 in FIG. 11. In FIG. 10, the secondary index assembly 146 is in the same angular position relative to the primary index assembly 144 as in FIG. 8, resulting in distal phalanxes 158, 160 being in the same position relative to the proximal phalanxes 154, 156 as in FIG. 9. In FIG. 10, the primary index assembly 144 and thumb assembly 142 are deflected inward by an angular movement corresponding to the positioning of the proximal phalanxes 154, 156, which brings the tips of the distal phalanxes 158, 160 together in a pinching motion.

Figure 12:
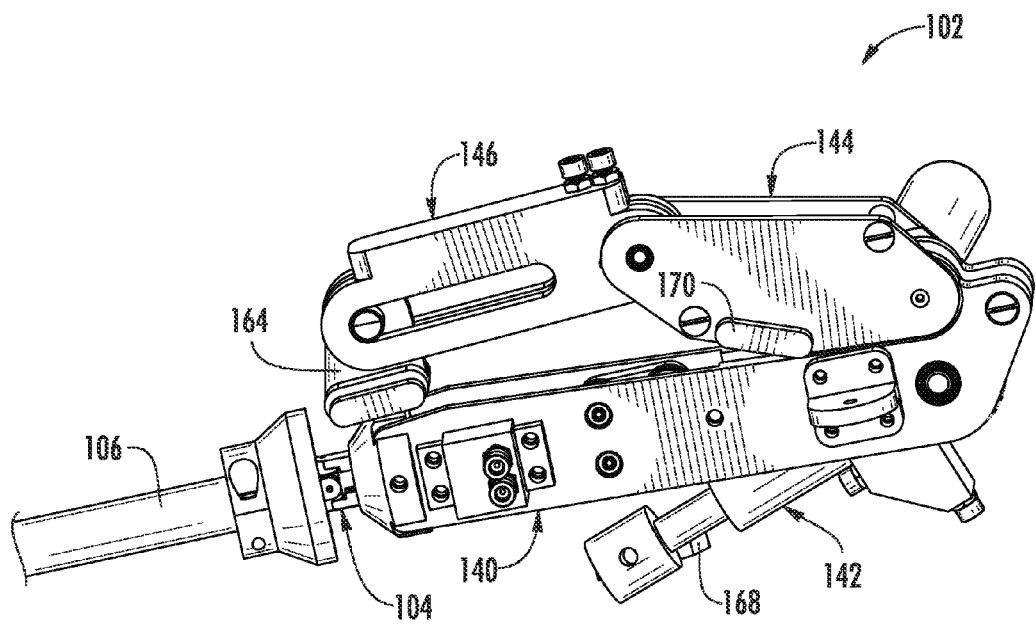
FIGS. 12 and 13 are left perspective views of the manipulator end portion and the end effector end portion, respectively, of the surgical tool shown in FIG. 1, in a corresponding fourth position.
Figure 13:
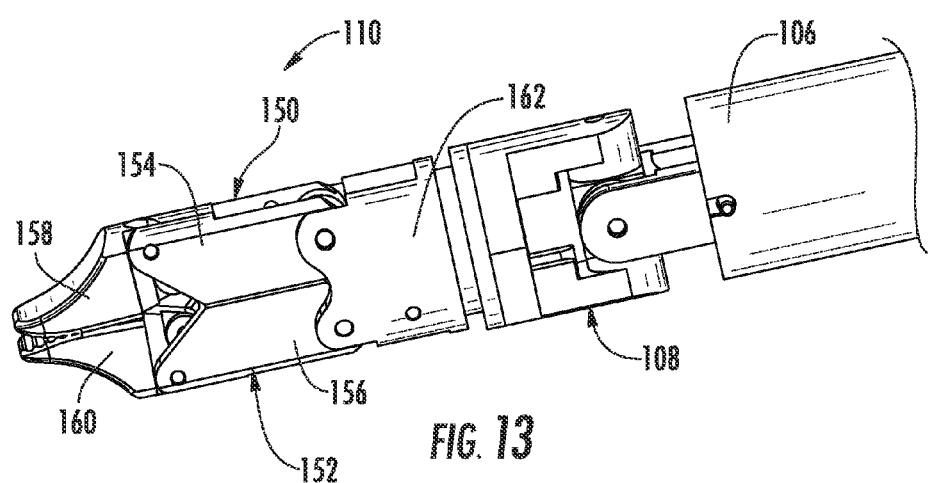

FIG. 12 shows the manipulator 102 in a position corresponding to the fully closed position of the end effector 110 in FIG. 13. In FIG. 12, the secondary index assembly 146 is deflected outward at the limit of its range of motion, as are the corresponding distal phalanxes 158, 160 of the end effector 110 in FIG. 13. In FIG. 12, the primary index assembly 144 and thumb assembly 142 are deflected inward to the limit of their ranges of motion, and accordingly so are the proximal phalanxes 154, 154 in the end effector 110 in FIG. 13.

Figure 14:
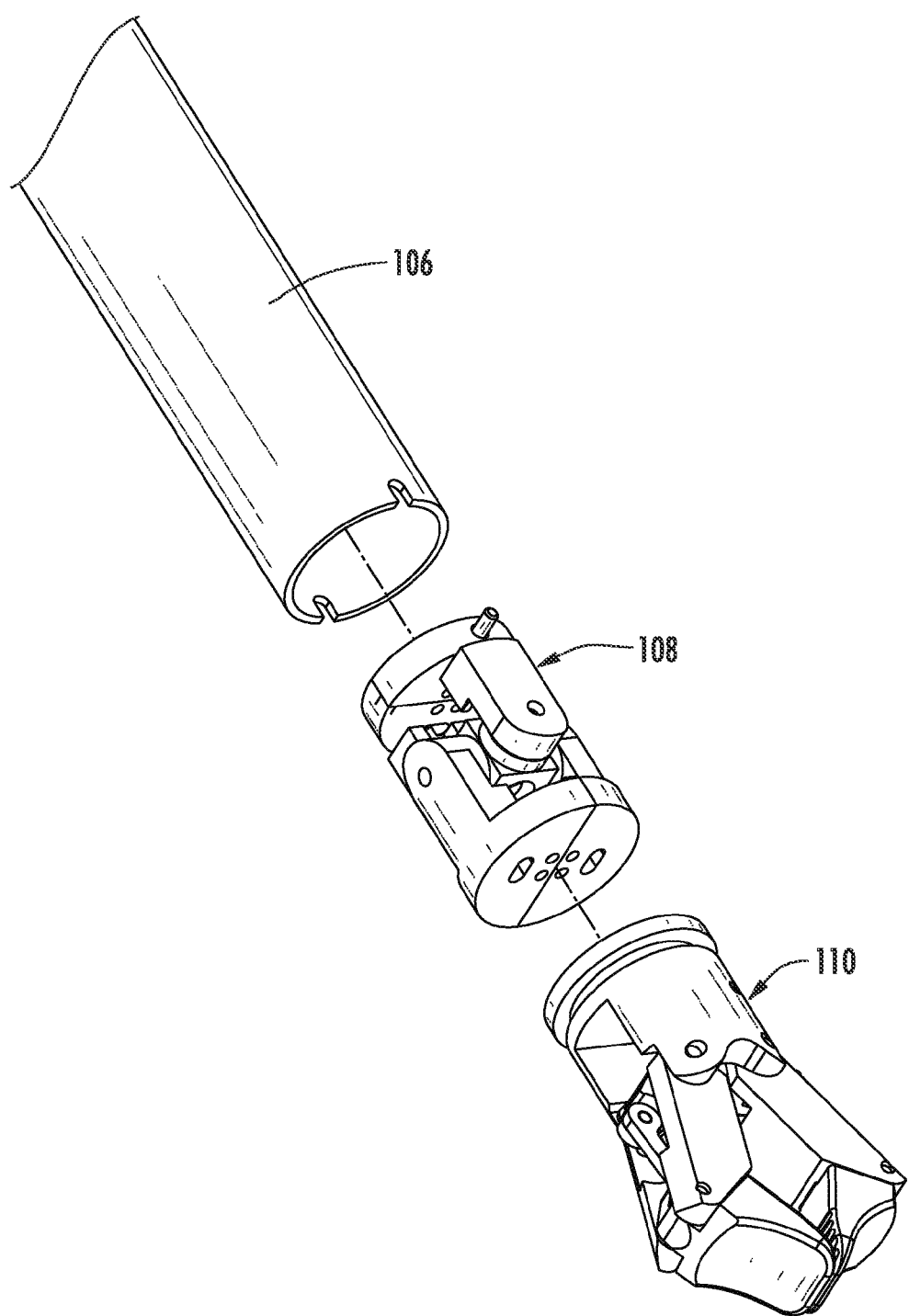
FIGS. 14 and 15 are exploded perspective views of the end effector end portion of the surgical tool shown in FIG. 1.
Figure 15:
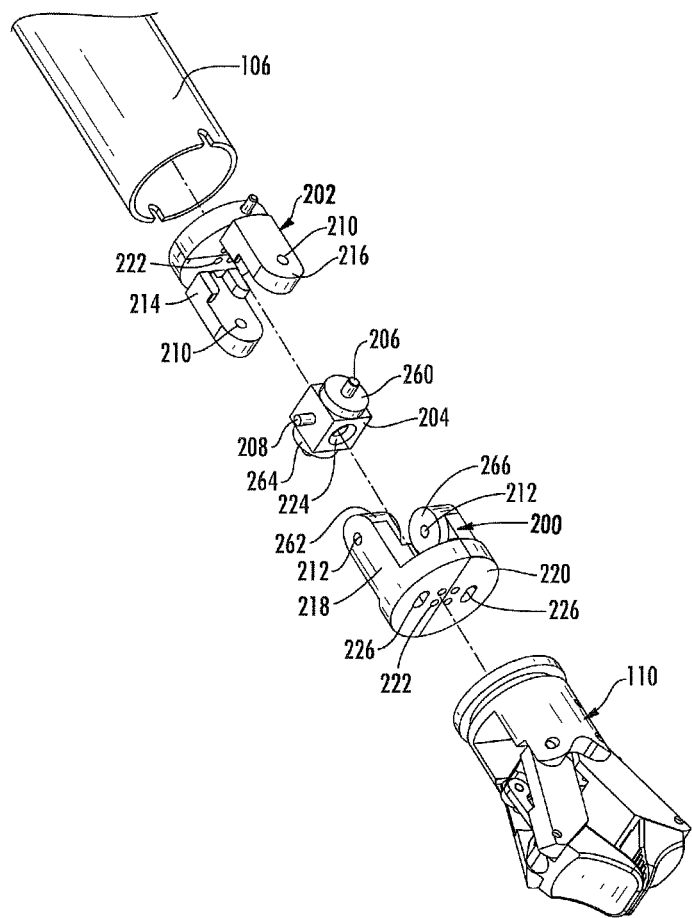

FIGS. 14 and 15 show the distal end of the embodiment of the surgical tool 100, where the distal universal joint 108 is mounted to the tube 108, and the end effector 110 is mounted to the distal universal joint 108. As shown in FIG. 15, in this embodiment the distal universal joint 108 includes a proximal yoke 202 and a distal yoke 200 in a perpendicular orientation. The yokes 200, 202 each include a base portion with two opposing arms extending substantially perpendicular to the base from the perimeter of the base. The yokes 200, 202 are mounted to a center block 204 with the ends of two perpendicular, coplanar pins 206, 208 disposed in holes 210, 212 in the yokes 200, 202. The center block 204 may be any shape that permits mounting of the yokes 200, 202 and concurrent pivoting about two axes. Pins 206, 208 may each include one or two pins or protrusions extending from the center block 204 as shown, or may be pins or protrusions formed in the arms of the yokes 200, 202 and extending into openings in the center block 204. For ease of manufacturing and assembly, each yoke 200, 202 may be made up of two halves 214, 216, 218, 220 as shown, or may be made of single pieces. Four holes 222 arranged about the center of the yokes 200, 202 and one larger hole 224 through the center of the center block 204 are provided to pass four cables (not shown) to control the end effector 110 from the manipulator 102, and two oblong shaped holes 226 are provided in the proximal and distal yokes 200, 202 to pass the cables for the universal joints 104, 108. In the embodiment of a surgical tool 100 shown, the proximal universal joint 104 is the same design as the distal universal joint 108, and as shown in FIG. 16 includes a proximal yoke 230, distal yoke 232, and center block 234.

Figure 16:
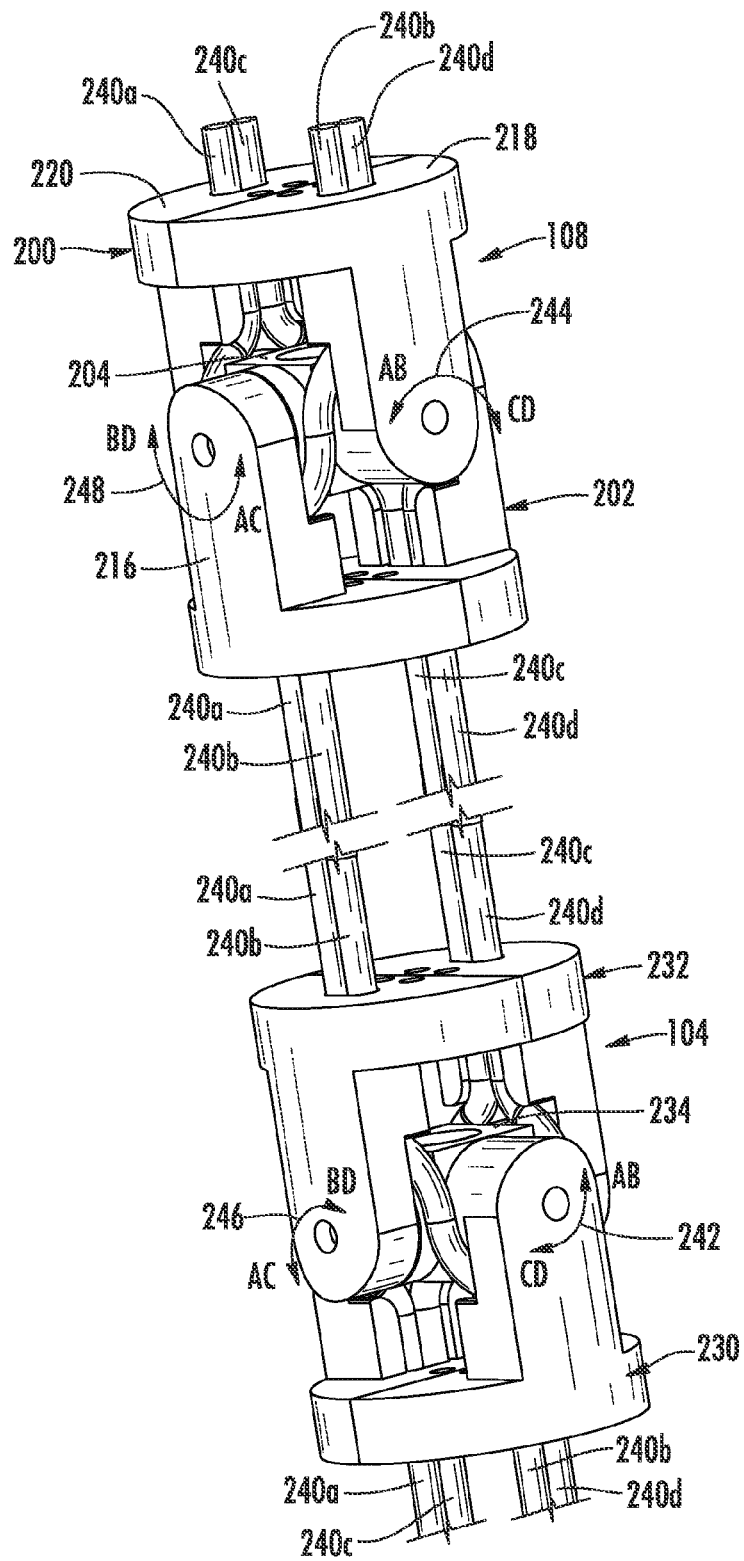
FIG. 16 is a perspective view of an articulation system of the surgical tool shown in FIG. 1, including embodiments of proximal and distal universal joints.
Figure 17:
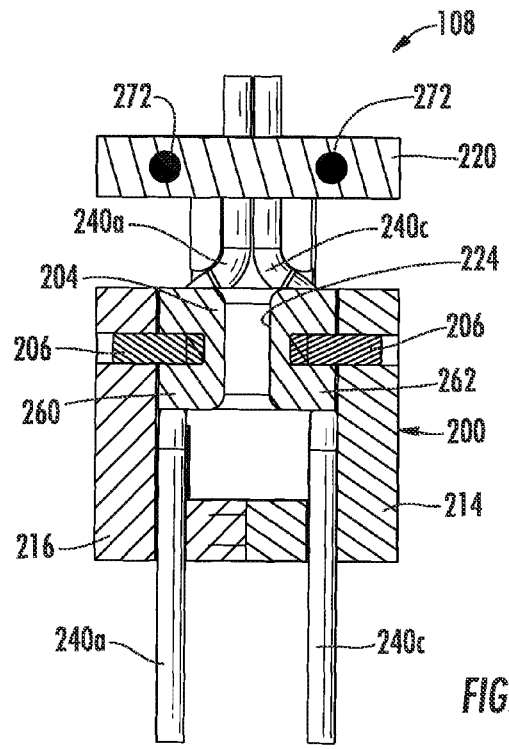
FIG. 17 is a cross section view of the distal universal joint assembly shown in FIG. 16.
Figure 18:
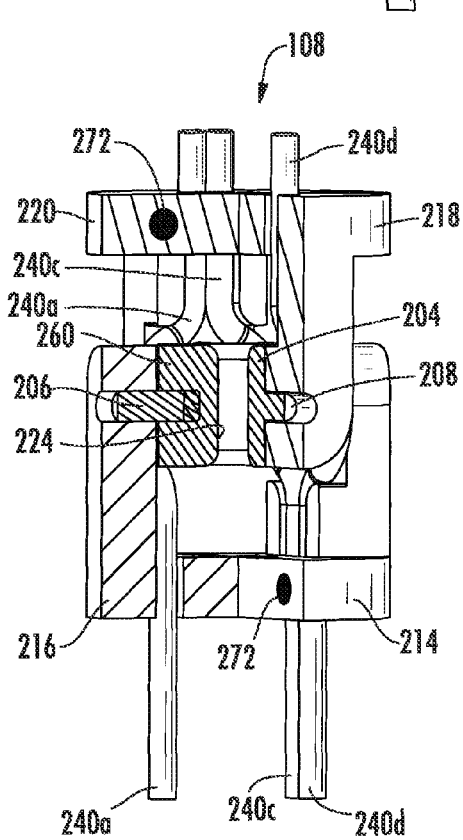
FIG. 18 is a partial section view of the distal joint assembly shown in FIG. 16, with a 90 degree wedge removed.
Figure 19:
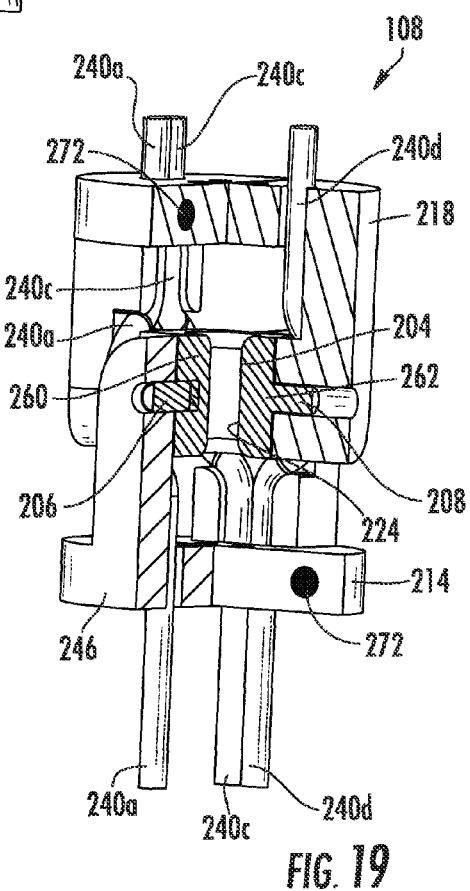
FIG. 19 is a partial section view of the distal universal joint assembly taken along the same lines as the section of FIG. 18, rotated for viewing another face of the section view.
Figure 23:
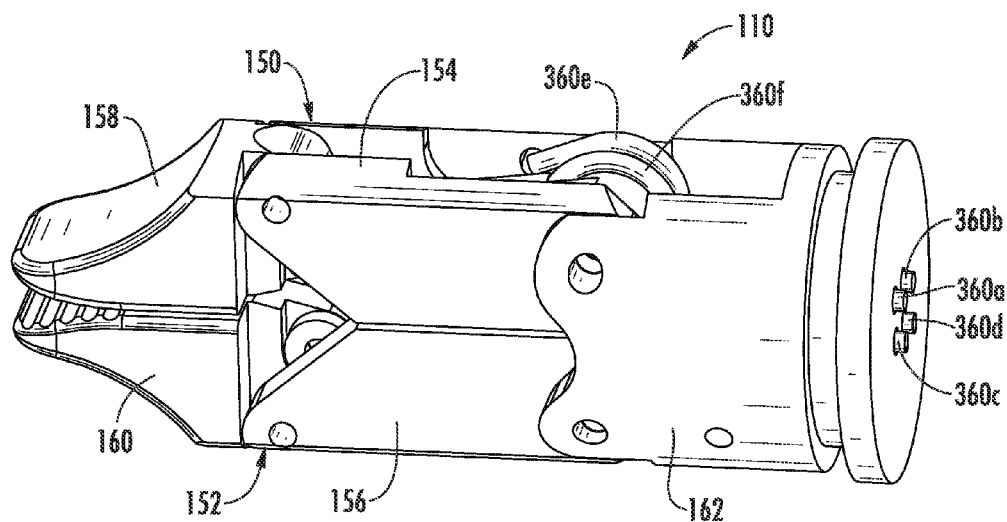
FIG. 23 is a left perspective view of the end effector shown in FIG. 14.

FIG. 16 further depicts the means by which the proximal universal joint 104 controls the distal universal joint 108. Four cables 240a, 240b, 240c, 240d connect the two joints 104, 108, are fixed at both ends, and control the motion of the universal joints 104, 108 about their two primary axes, as established, for example, by the pins 206, 208 (FIG. 15) in the distal universal joint 108. At the distal end of the more distal yoke 200, this can be accomplished at the distal universal joint 108 with means including, but not limited to, adhesive, swaged components, or other friction fit-based mechanism. Cables 240a and 240c may each may be one cable that doubles back distal of the distal yoke 200, as may cables 240b and 240d, or they may be separate cables as shown. Regardless of whether they are separate or a single cable, the cables are all in a fixed position at the distal point of the distal yoke 200. With respect to the proximal universal joint 104, the ends of the cables 240a, 240b, 240c, 240d are fixed via a set of tensioning assemblies in the manipulator 102, discussed further below. This allows the relative positioning of the proximal and distal universal joints 104, 108 to be calibrated during manufacturing.

Exemplary operational scenarios are as follows. When the distal yoke 232 of the proximal universal joint 104 pivots 242 about the proximal center block 234 in a clockwise direction (designated CD), then cables 240c and 240d are displaced downward and cables 240a and 240b are displaced upward. This produces a similar pivot 244 in the clockwise direction CD of the distal yoke 200 of the distal universal joint 108 about the distal center block 204. With respect to rotation in a perpendicular plane to motion 242, when the distal yoke 232 of the proximal universal joint 104 causes the proximal center block 234 to rotate 246 relative to the proximal yoke 230 in a clockwise direction (designated BD), cables 240b and 240d are displaced downward and cables 240a and 240c are displaced upward. This produces a similar pivot 248 in the clockwise direction BD of the distal center block 204 relative to the proximal yoke 202.

Motion 246 in counterclockwise direction AC in the proximal universal joint 104 likewise causes motion 248 in counterclockwise direction AC in the distal universal joint 108, and motion 242 in counterclockwise direction AB in the proximal universal joint 104 causes motion 244 in counterclockwise direction AB in the distal universal joint 108. The various motions may be combined. The mounting of the proximal yoke 230 of the proximal universal joint 104 to the distal end of the manipulator 102 results in the movement of the manipulator 102 causing the movement of that yoke 230. All motions of the proximal yoke 230 of the proximal universal joint 104 actuate cables 240a, 240b, 240c, 240d to produce similar motion in the opposite direction in the distal yoke 200 of the distal universal joint 108.

FIGS. 17-21 depict a universal joint with the cabling system that drives both the proximal and distal universal joints 104, 108. Although it is the distal universal joint 108 that is shown, this could be the proximal universal joint 104, and the proximal and distal universal joints 104, 108 generally mirror each other in their configuration about a plane perpendicular to the cabling and between the joints 104, 108.

When the universal joint 108 is assembled, there are round members on each side of the center block 204 in a parallel plane to the adjacent center block sides. The four round members 260, 262, 264, 266 (FIG. 15), which may be part of the center block 204, part of the yokes 200, 202, or independent parts, are used to route the cables 240a, 240b, 240c, 240d to impart force on the joint 108 when the cables are displaced. In FIG. 20, one yoke half 214 is removed to show the cabling system, and all four cables 240a, 240b, 240c, 240d may be seen at least in part inside the joint 108 in FIG. 21. Pins 270 and holes to receive the pins 272 may be used to hold the yoke halves 214, 216, 218, 220 together. Cable 240b passes through the proximal yoke 200 and around the bottom of a first round member 260, over the top of a second round member 262 and into the distal yoke 202. Cable 240a opposes cable 240b in controlling the rotation of the center block 204 about the axis of the first round member 260, coincident with pins 206 (and motion 248 of FIG. 16). Cables 240c and 240d behave similarly with respect to this movement. Cable 240b opposes cable 240d in controlling the rotation of the distal yoke 202 about the axis of the second round member 262, coincident with pins 208 (and motion 244 of FIG. 16). Cables 240a and 240c behave similarly with respect to this movement.

FIGS. 22-26 show an embodiment of an end effector 110. This end effector includes the proximal phalanxes 154, 156 mounted to the base member 162 with pins 300, 302. Pulleys 304, 306 are mounted with a pin 308 near the proximal end within the base member 162. Each digit 150, 152 contains a controlling link 310, 312 which is connected to a connecting link 314, 316 with pins 318, 320, and the connecting links 314, 316 are connected to the distal phalanxes 158, 160 with pins 322, 324. The distal phalanxes 158, 160 are also mounted to the proximal phalanxes 154, 156 with pins 326, 328.

Figure 24:
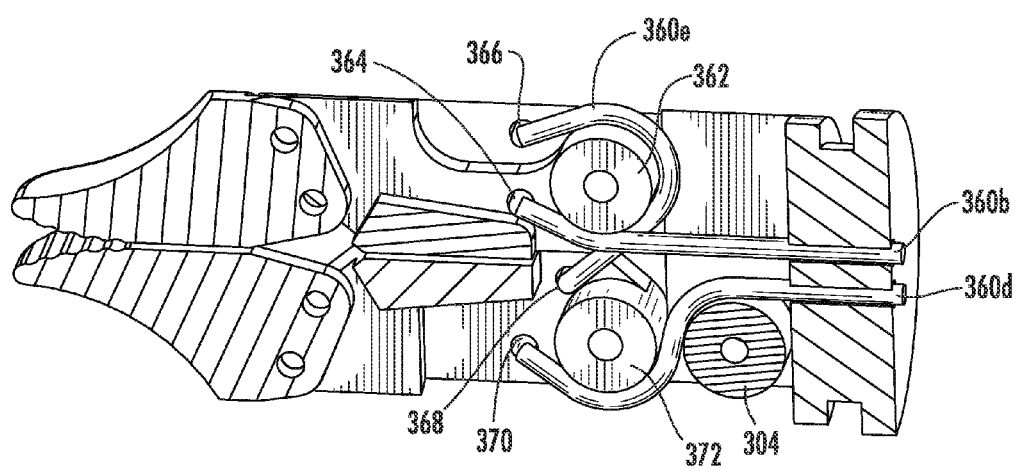
FIG. 24 is longitudinal section perspective view of the end effector shown in FIG. 14, taken from the view of FIG. 23.
Figure 25:
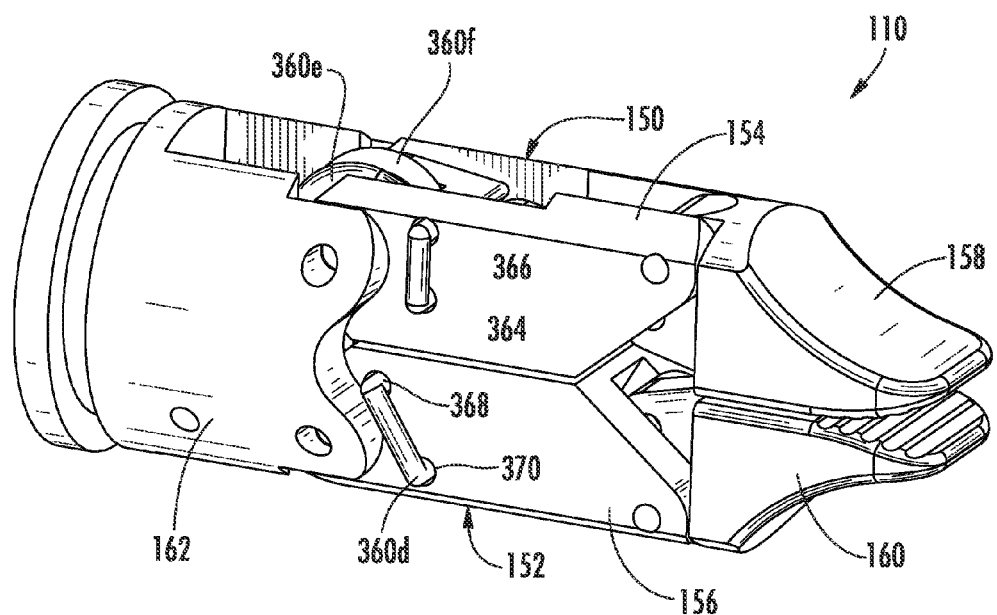
FIG. 25 is a right perspective view of the end effector shown in FIG. 14.

FIG. 24 illustrates the cabling system and structure controlling the motion of the proximal phalange 154, 156 of each digit 150, 152, where cable 360b controls closing and cable 360d controls opening. The pulley 304 guides cable 360d to maintain it with the other end effector control cables 360a, 360b, 360c in the center of the base member 162. Cables 360b and 360d are different ends of the same physical cable in the preferred embodiment, but may be separate cables in another embodiment and are functionally distinct. Cable 360b passes around a pulley section 362 built into the proximal phalange 154 of the first digit 150 and enters a hole 364 that secures cable 360*b* to the proximal phalange 154 of the first digit 150. Cable 360*b* continues back through a second hole 366 in the proximal phalange 154 of the first digit 150, around the pulley section 362 in this phalange 154, and subsequently enters a hole 368 that secures it to the proximal phalange 156 of the second digit 152. The section of cables 360*b* and 360*d* between the points of fixation 364, 368, which joins the proximal phalanxes 154, 156 will be denoted cable 360*e*. Cable 360*e* couples the motion of the proximal phalanxes 154, 156 such that their motion mirrors each other. The cable 360*d*, with the designation starting at hole 368, returns through a second hole 370 in the proximal phalange 156 of the second digit 152, passes around a pulley section 372 of that phalange 156, around the guide pulley 304, and exits through the base 162.

The attachment points where the length of cable 360*e* is secured to the phalanxes 154, 156 may be created by a combination of friction due to the cable turning tightly at the entry and exit points of these holes 364, 368, as well as adhesive that may be used to secure the cable 360*e*. The connection may also be created by other means, for example, through friction via a swaging of the first phalanxes 154, 156 at cable entry and exit points, or through an additional component that applies pressure to the cable, creating friction between the cable and the phalanxes 154, 156.

When cable 360*b* is pulled towards the manipulator 102, this exerts a torque on the proximal phalange 154 of the first digit 150 in a counterclockwise direction. This in turn exerts a force on cable 360*e*, which exerts a clockwise torque on the proximal phalange 156 of the second digit 152. The effect of these torques is to bring the proximal phalanxes 154, 156 together. When cable 360*d* is pulled, this exerts a torque on the proximal phalange 156 of the second digit 152 in a counterclockwise direction. This in turn exerts a force on cable 360*e*, which exerts a clockwise torque on the proximal phalange 154 of the first digit 150. The effect of these torques is to separate the proximal phalanxes 154, 156, pulling the digits open. In this manner, cables 360*b* and 360*d* control the opening and closing motion of this embodiment of the end effector 110.

Figure 26:
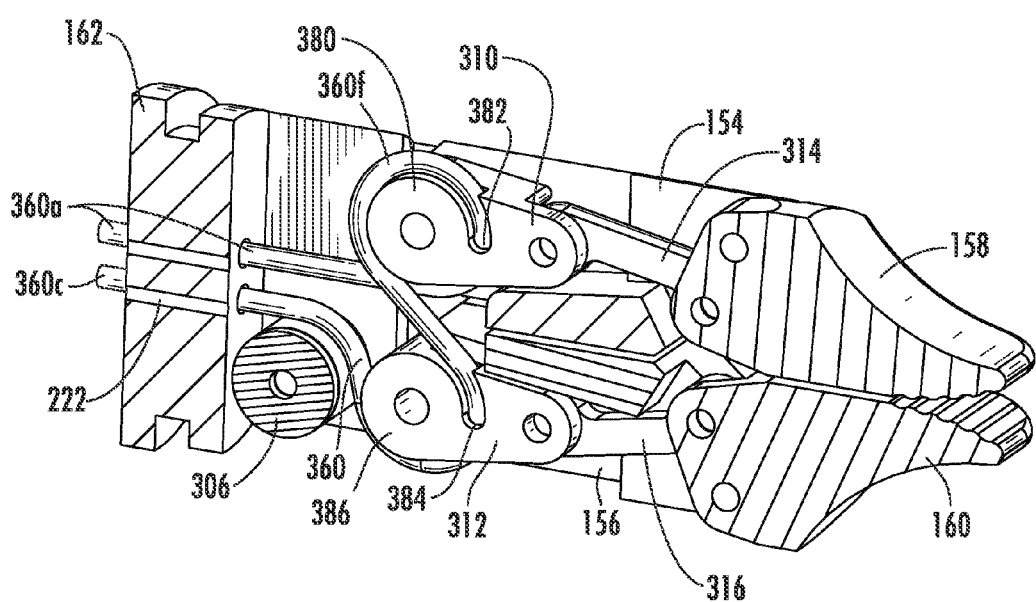
FIG. 26 is longitudinal section perspective view of the end effector shown in FIG. 14, taken from the view of FIG. 25.

FIG. 26 shows the cabling system that controls the four bar mechanisms within each digit 150, 152 of the end effector 110. Each digit 150, 152 includes a controlling link 310, 312 that moves a connecting link 314, 316 to actuate the distal phalanxes 158, 160 of the fingers in the end effector 110. The cabling system that drives the controlling links 310, 312 includes cables 360*a* and 360*c*. Cable 360*a* passes around the pulley section 380 in the first controlling link 310 in the proximal digit 150 of the end effector 110 and into a hole 382 where it is secured to the first controlling link 310. The cable 360*a* then continues around the pulley section of the first controlling link 310, departing the first controlling link 310 and connecting to the second controlling link 312, passing through a hole 384 that secures it to the second controlling link 312. The section of cable between holes 382 and 384 will be referred to as cable 360*f*. From hole 384, the cable 360*c* continues around the pulley section 386 of the second controlling link 312, goes around the guide pulley 306 and exits through the base member 162. The attachment between cable 360*a*, 360*c*, and 360*f* and the controlling links 310, 312 may be achieved through any of the methods previously described for the proximal phalanxes 154, 156.

When cable 360*a* is pulled, it exerts a torque on the first controlling link 310 in the clockwise direction. This exerts a force on cable 360*f*, which in turn exerts a counterclockwise torque on the second controlling link 312. This causes both controlling links 310, 312 to move inward. When cable 360*c* is pulled, it exerts a torque on the second controlling link 312 in the clockwise direction. This exerts a force on cable 360*f*, which in turn exerts a counterclockwise torque on the first controlling link 310. This causes both controlling links 310, 312 to move outward.

Figure 27:
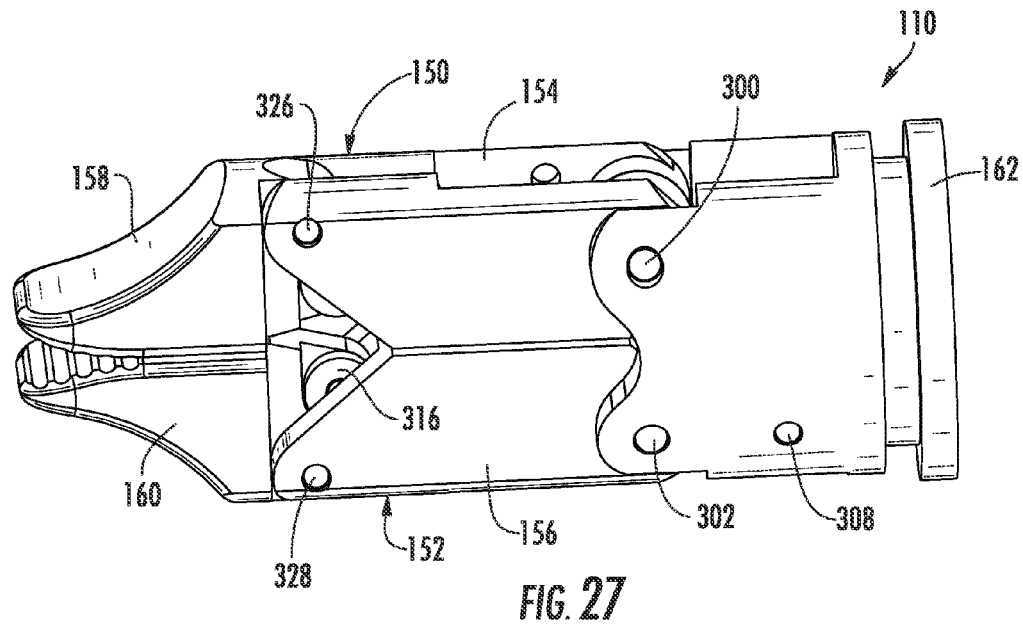
FIG. 27 is a left perspective view of the end effector shown in FIG. 14, with the end effector in a first position.
Figure 28:
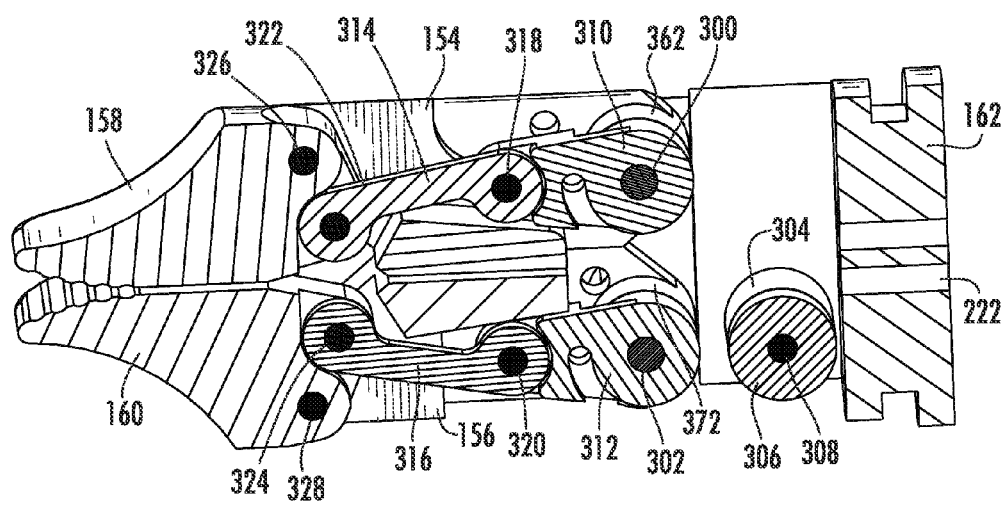
FIG. 28 is longitudinal section perspective view of the end effector shown in FIG. 14, taken offset from center and in the same position as in the view of FIG. 27.

FIGS. 27-34 show the end effector 110 in several positions. FIGS. 27 and 28 show the end effector 110 in its closed position. With respect to the first digit 150, the controlling link 310 pivots on a pin 300 to actuate the associated connecting link 314 via pin 318. The connecting link 314 in the first digit 150 controls the associated distal phalange 158 via a pin 322. The distal phalange 158 pivots relative to the proximal phalange 154 via a pin 326. Similarly, with respect to the second digit 152, the controlling link 312 pivots on a pin 302 to actuate the connecting link 316. The controlling link 312 controls the connecting link 316 via a pin 320. The connecting link 316 in the second digit 152 controls the distal phalange 160 via a pin 324. The distal phalange 160 pivots relative to the proximal phalange 156 via a pin 328. The guide pulleys 304, 306 pivot about a pin 308.

Figure 29:
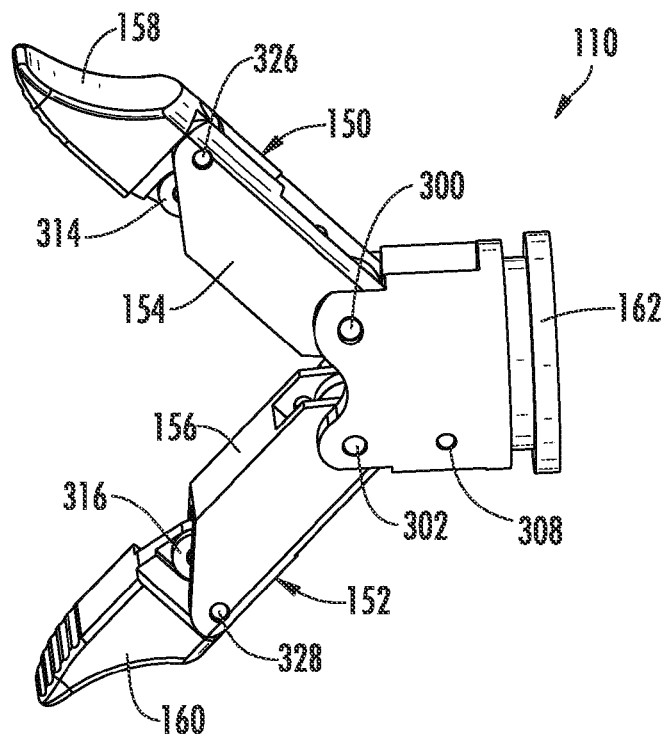
FIG. 29 is a left perspective view of the end effector shown in FIG. 14, with the end effector in a second position.
Figure 30:
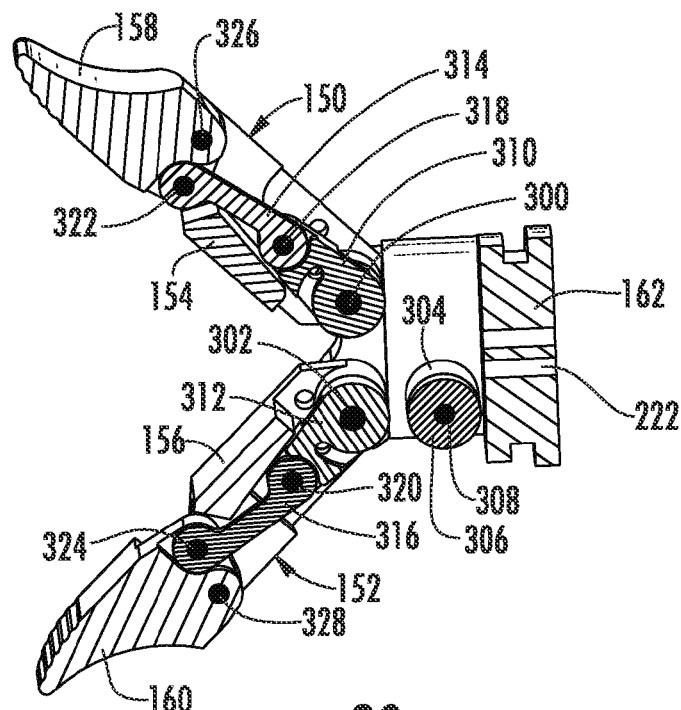
FIG. 30 is longitudinal section perspective view of the end effector shown in FIG. 14, taken offset from center and in the same position as in the view of FIG. 29.

The end effector 110 is shown in the fully open position in FIGS. 29 and 30. In order to obtain this position, the controlling links 310, 312 move outward with their respective proximal phalanxes 154, 156. This produces no movement of the distal phalanxes 158, 160 relative to the proximal phalanxes 154, 156 of each digit 150, 152.

Figure 31:
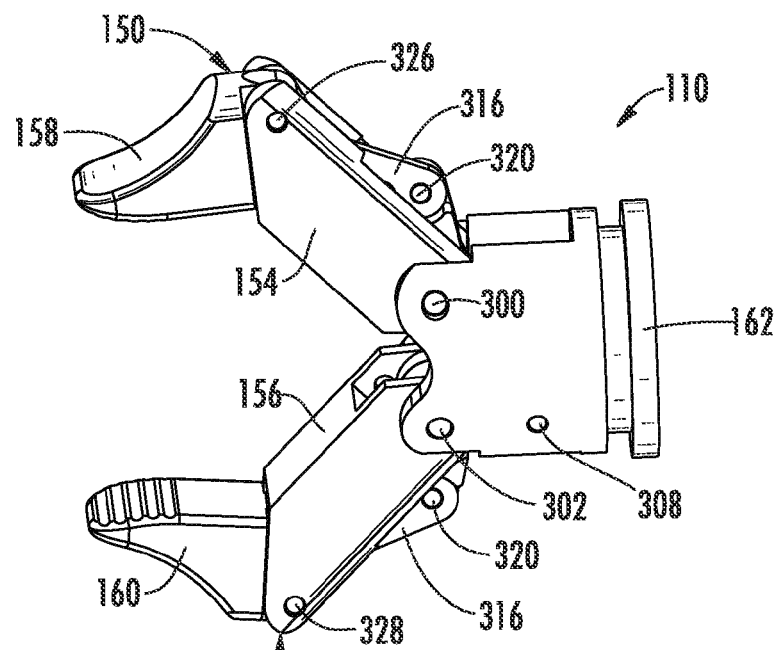
FIG. 31 is a left perspective view of the end effector shown in FIG. 14, with the end effector in a third position.
Figure 32:
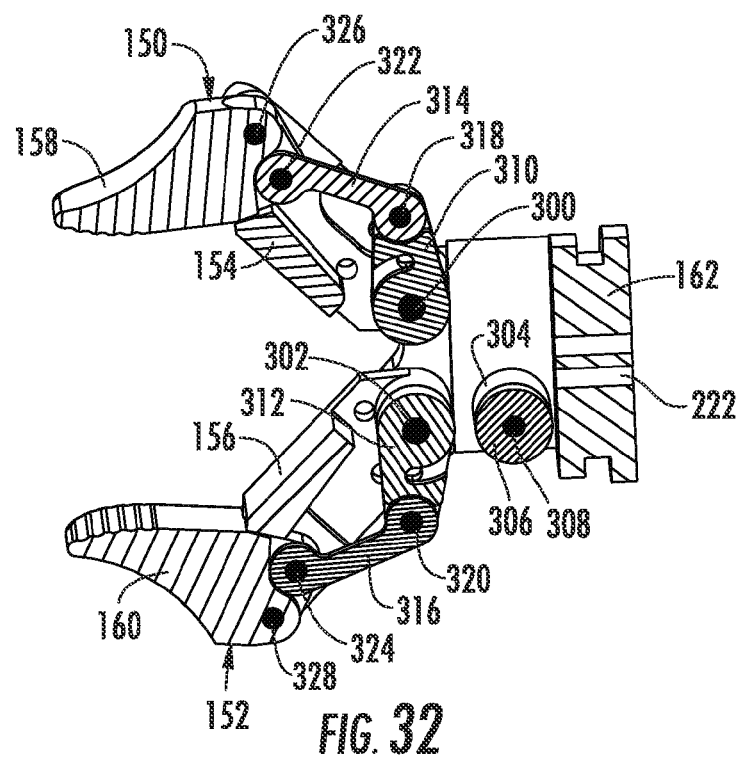
FIG. 32 is longitudinal section perspective view of the end effector shown in FIG. 14, taken offset from center and in the same position as in the view of FIG. 31.

FIGS. 31 and 32 show the end effector 110 in its open gripping position. This can be utilized for grasping or retracting larger tissue structures or organs. In order to obtain this position, the controlling links 310, 312 move outward beyond their respective proximal phalanxes 154, 156 to produce motion of the connecting links 314, 316, subsequently causing the distal phalanxes 158, 160 to deflect inward. The motion of the controlling links 310, 312 relative to the proximal phalanxes 154, 156 thus controls the motion of the distal phalanxes 158, 160 relative to the proximal phalanxes 154, 156 of each digit 150, 152.

Figure 33:
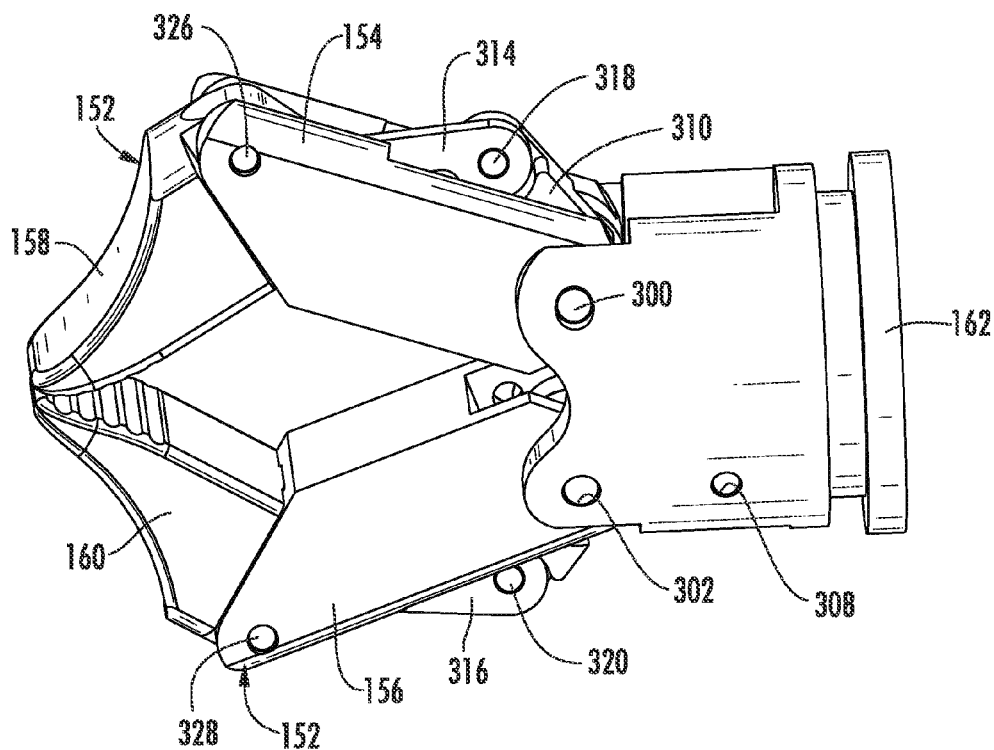
FIG. 33 is a left perspective view of the end effector shown in FIG. 14, with the end effector in a fourth position.
Figure 34:
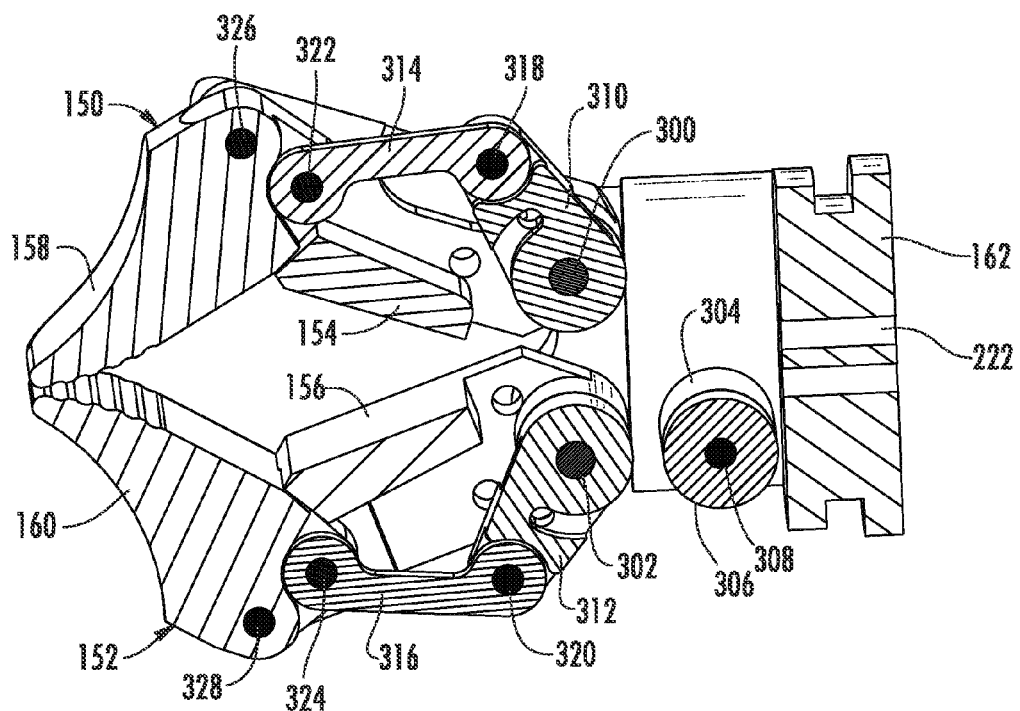
FIG. 34 is longitudinal section perspective view of the end effector shown in FIG. 14, taken offset from center and in the same position as in the view of FIG. 33.

FIGS. 33 and 34 show the end effector 110 in its pinching position. This can be utilized to exert higher gripping pressure on denser tissue structures for grasping or retraction. In order to obtain this position, the controlling links 310, 312 are deflected outward relative to their respective proximal phalanxes 154, 156 as in the open gripping position, but the proximal phalanxes 154, 156 are not outwardly deflected to the extent that they are in the open gripping position.

Figure 35:
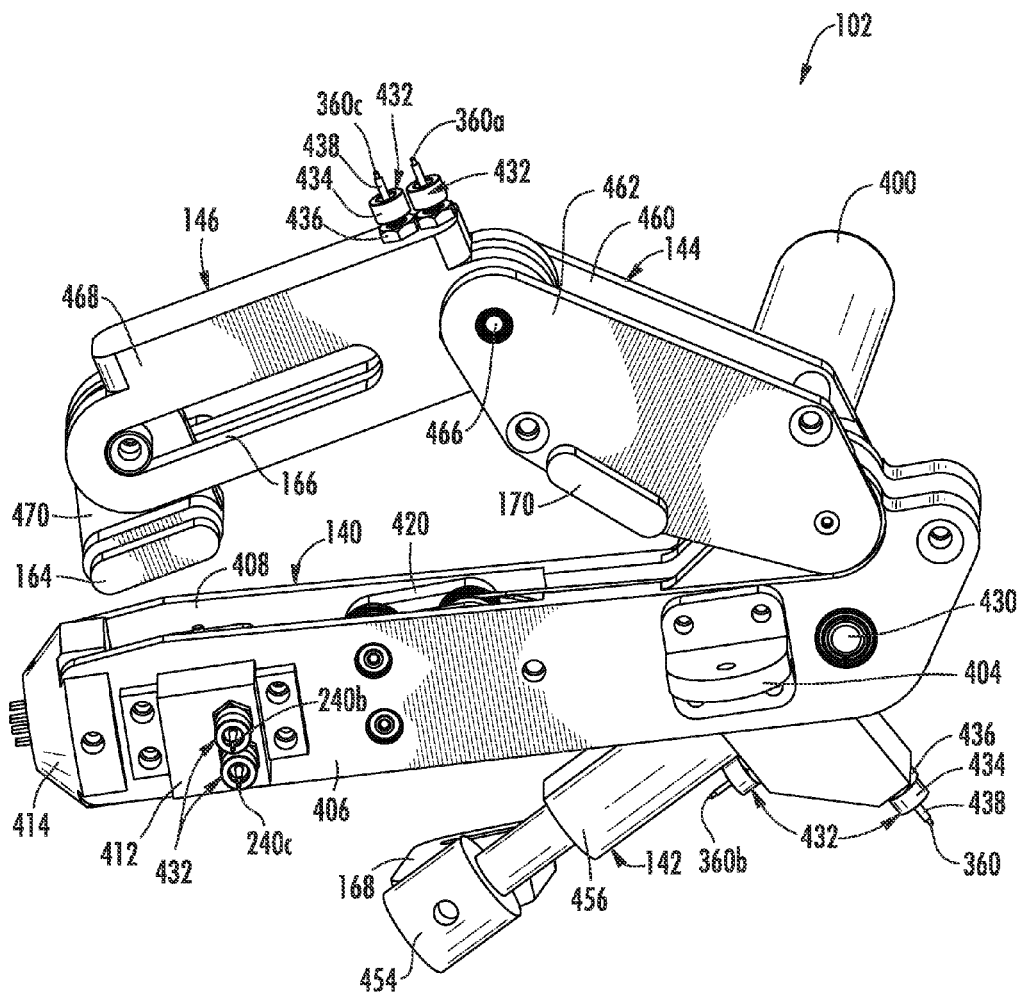
FIG. 35 is a left perspective view of an embodiment of a manipulator as shown in FIG. 1.
Figure 36:
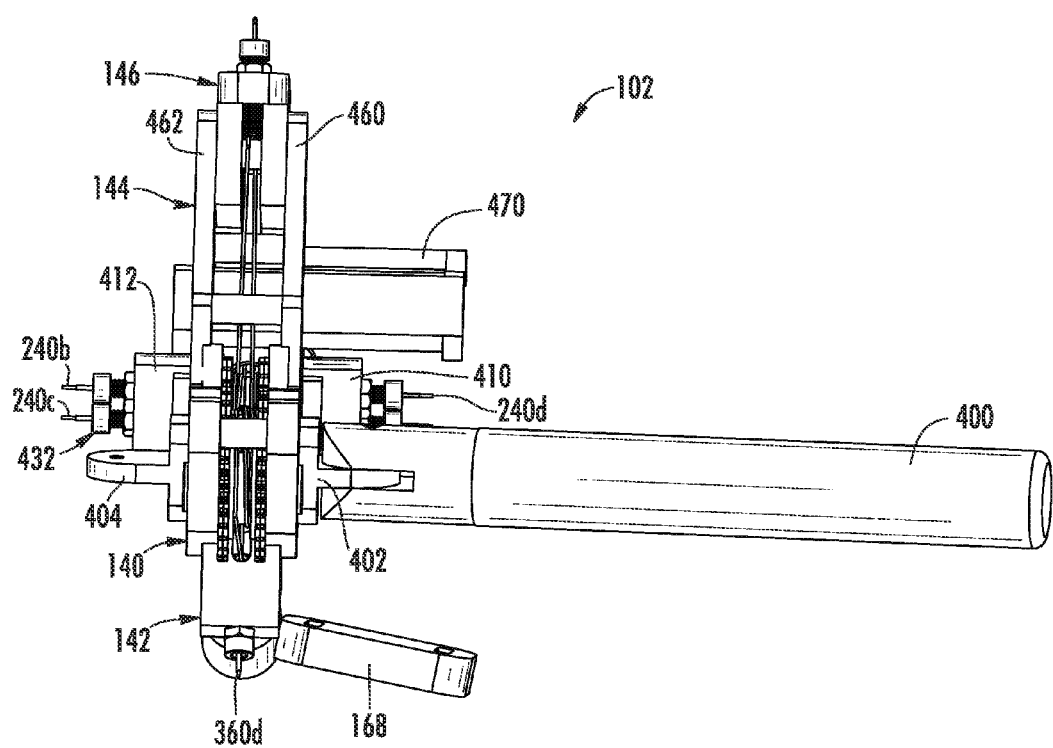
FIG. 36 is a back elevation view of the manipulator shown in FIG. 35.
Figure 37:
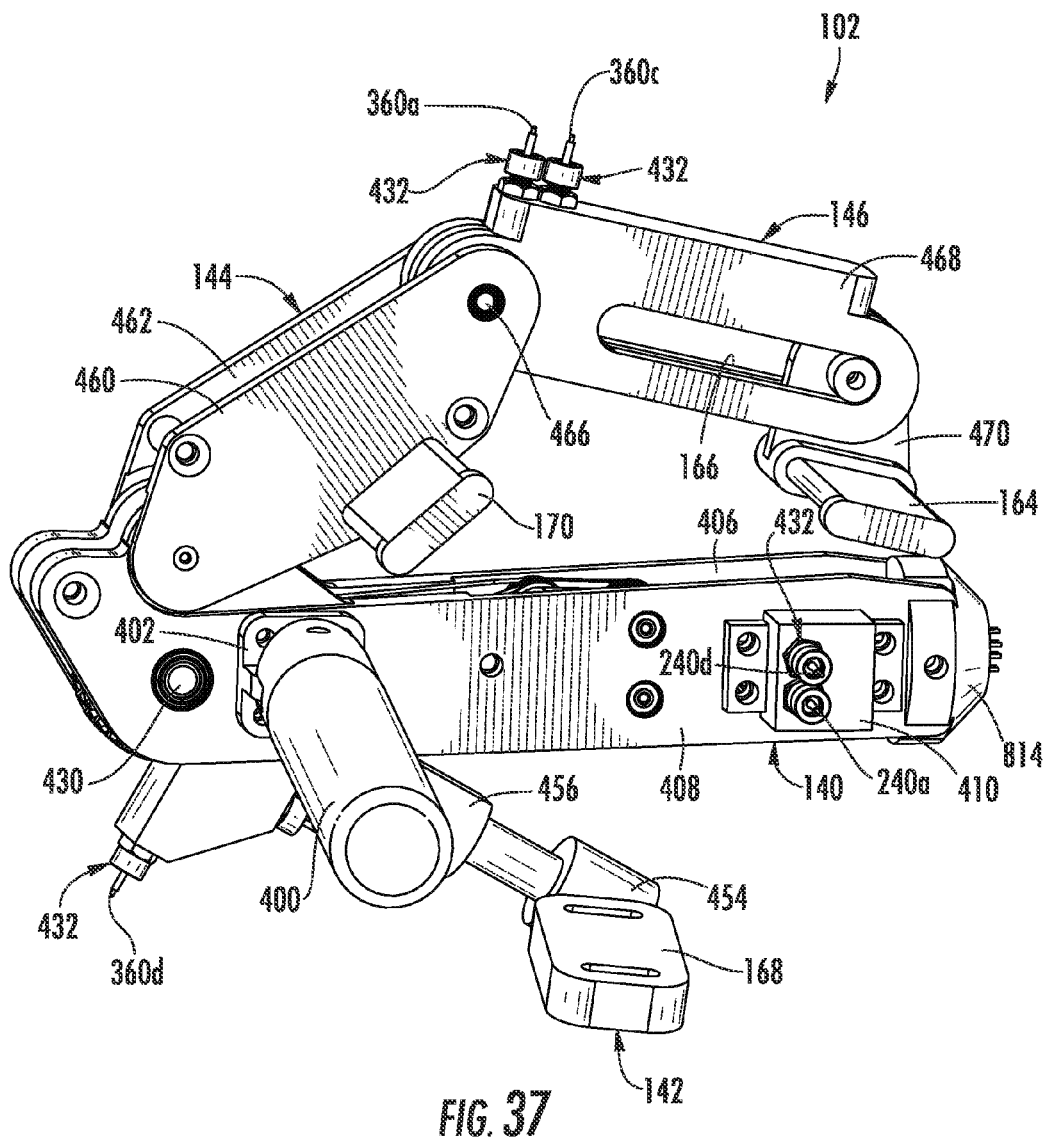
FIG. 37 is a right perspective view of the manipulator shown in FIG. 35.
Figure 38:
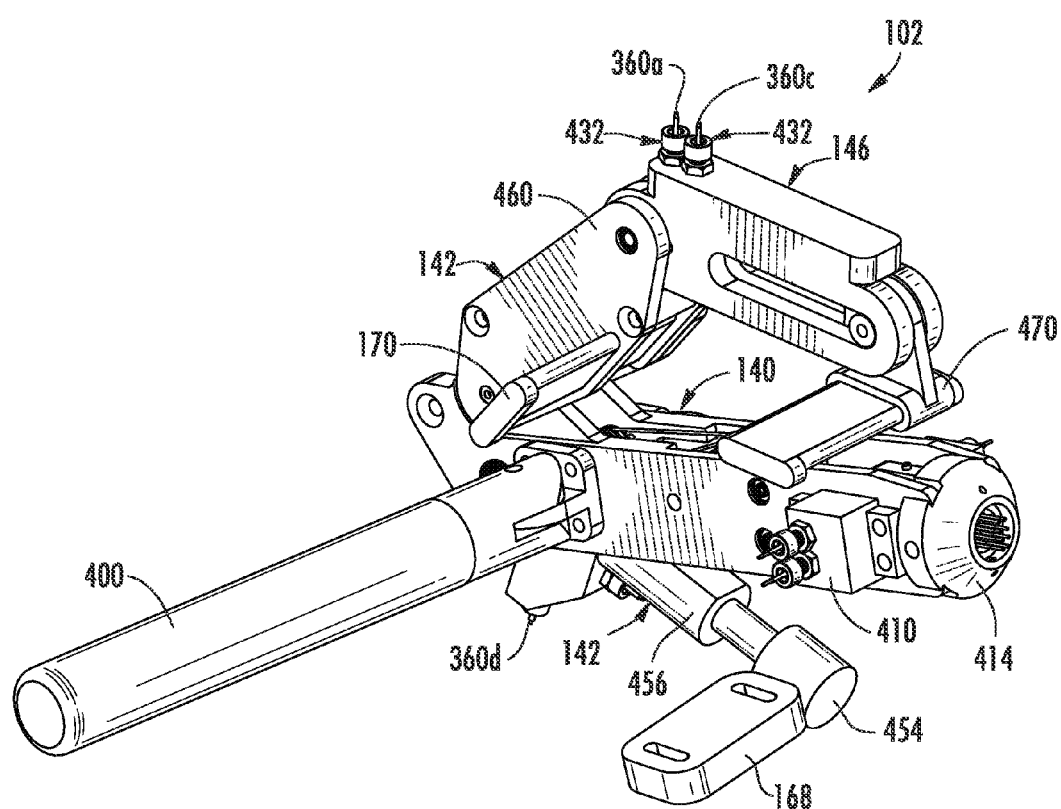
FIG. 38 is a front right perspective view of the manipulator shown in FIG. 35.

FIGS. 35-41 show the manipulator 102 in various views. The handlebar 400 may be gripped by the third, fourth, and fifth fingers of the user, providing stable control and allowing the user to apply torsion to the manipulator 102. The handlebar 400 attaches to the base assembly 140 at the handlebar mount 402. FIG. 35 also shows the alternate handlebar mount 404. The manipulator 102 in FIGS. 35-41 is in a right-handed configuration. If the handlebar 400 were attached to the alternate handlebar mount 404, it would be in a left-handed configuration. All other points at which the user's hand attaches to the manipulator 102 can be changed to a left-handed configuration via rotation or sliding.

Figure 39:
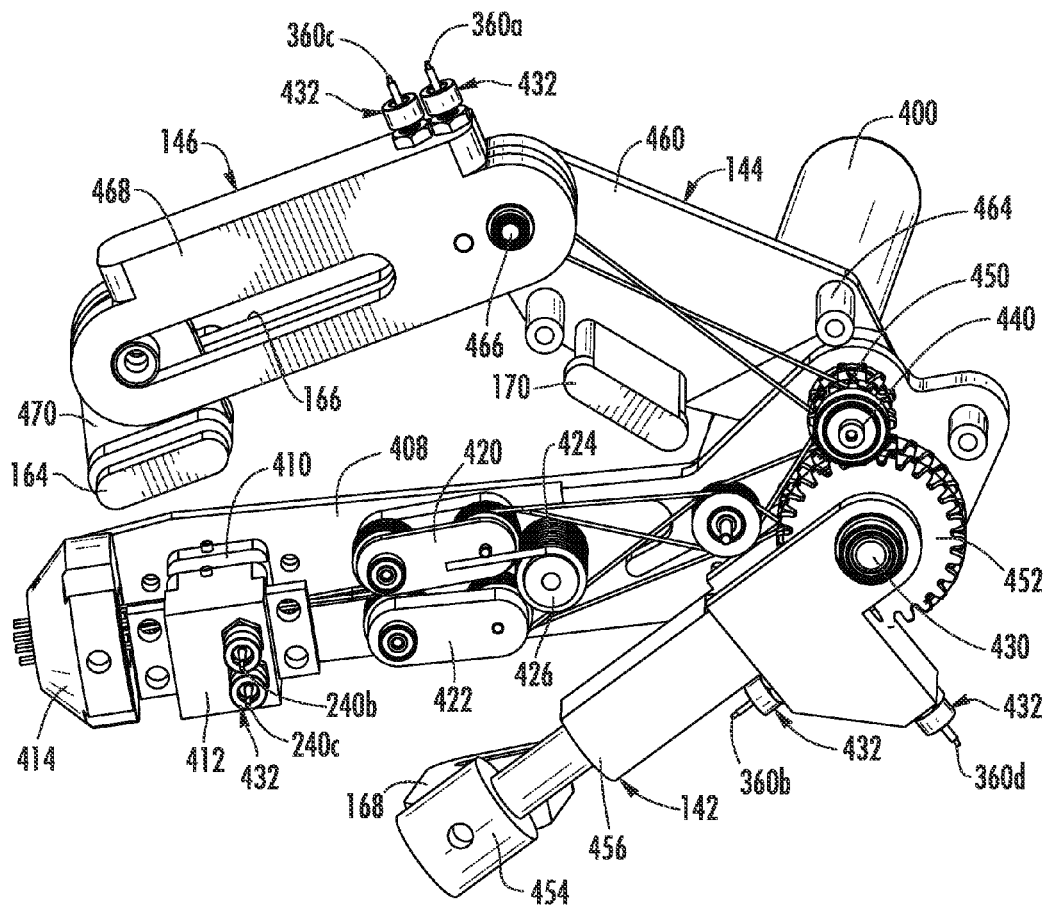
FIG. 39 is an exposed left perspective view of the manipulator shown in FIG. 35.

FIG. 39 shows the manipulator 102 with the alternate handlebar mount 404 and one base plate 406 of the two base plates 406, 408 removed. The cabling system for controlling the end effector 110 and the tensioning assemblies 410, 412 for calibrating the relative position of the proximal and distal universal joints 104, 108 can be seen in this figure, as well as the method by which the thumb assembly 142, primary index assembly 144, and secondary index assembly 146 control the end effector 110. The end effector control cables 360*a*, 360*b*, 360*c*, 360*d* (cables not labeled in FIG. 39) enter the manipulator 102 through the universal joint interface 414 and continue to the active tensioning assemblies 420, 422 which are tensioned by a spring 424 mounted on a spacer 426. The end effector control cables 360*a*, 360*b*, 360*c*, 360*d* then pass around the guide pulley set 428.

The cables 360*b*, 360*d* that control the motion of the proximal phalanxes 154, 156 of the end effector 110 are then anchored to the thumb assembly 142 that pivots about a pin 430 attached to the base assembly 140 with bearings. This anchoring is achieved by means of a tension adjusting system 432 used in several locations that includes vented screws 434, nuts 436, and swaged tubing 438, as identified with the ends of cables 360*c* and 360*d* in FIG. 35. The swaged tubing 438 is compressed onto the control cables to act as mechanical retention against the head of the vented screws 434. Tension is applied to the control cables by rotating the nut 436 while keeping the corresponding vented screw 434 in a constant rotational position. This produces linear translation of the vented screw 434 and a corresponding change in tension in its control cable.

The cables 360*a*, 360*c* that control the motion of the distal phalanxes 158, 160 pass around an idling pulley set mounted on a set of shaft adapters 440 and continue to the secondary index assembly 146. These cables 360*a*, 360*c* are connected to the secondary index assembly 146 by means of the tension adjusting system 432 similar to that used for cables 360*b* and 360*d*.

The primary index assembly 144 and thumb assembly 142 are mechanically coupled by means of a set of gears 450, 452. This allows the thumb and index finger of the user to collectively drive the proximal phalanxes 154, 156. The thumb assembly 142 adjusts to different hand sizes. This is accomplished by a set of moving elements; the thumb slide 454 which translates and rotates within the thumb base 456, and the thumb mount 168 which rotates within the thumb slide 454. The linear translation of the thumb slide 454 compensates for thumbs of different lengths. The rotation of the thumb slide 454 and thumb mount 168 allows the manipulator 102 to change into a left-handed configuration from the right-handed configuration depicted in FIG. 35-41.

The primary index assembly 144 pivots about the set of shaft adapters 440 via a set of bearings in the base plates 406, 408. The primary index assembly 144 includes two base plates 460, 462 one of which 462 is removed in FIG. 39. These plates 460, 462 are connected by spacers 464. The primary index mount 170 may attach to the user's index finger (the portion of primary index mount 170 to which a user's finger is attached is not visible in FIG. 39). The primary index mount 170 can translate laterally through the primary index assembly 144 to change the manipulator 102 from the right-handed configuration depicted in FIGS. 35-41 to a left-handed configuration.

The secondary index assembly 146 pivots about a shaft 466 via a set of bearings in the primary index base plates 460, 462. The secondary index base 468 contains the index slide 470 that can translate and rotate within the secondary index base 468. The index slide 470 contains the index mount 164 that is the attachment point for the tip of the user's index finger and can translate laterally through the index slide 470 to change the manipulator 102 from the right-handed configuration depicted in FIGS. 35-41 to a left-handed configuration. The index slide 470 translates along the secondary index base 468 in the slot 166 to adjust to different length index fingers.

Figure 40:
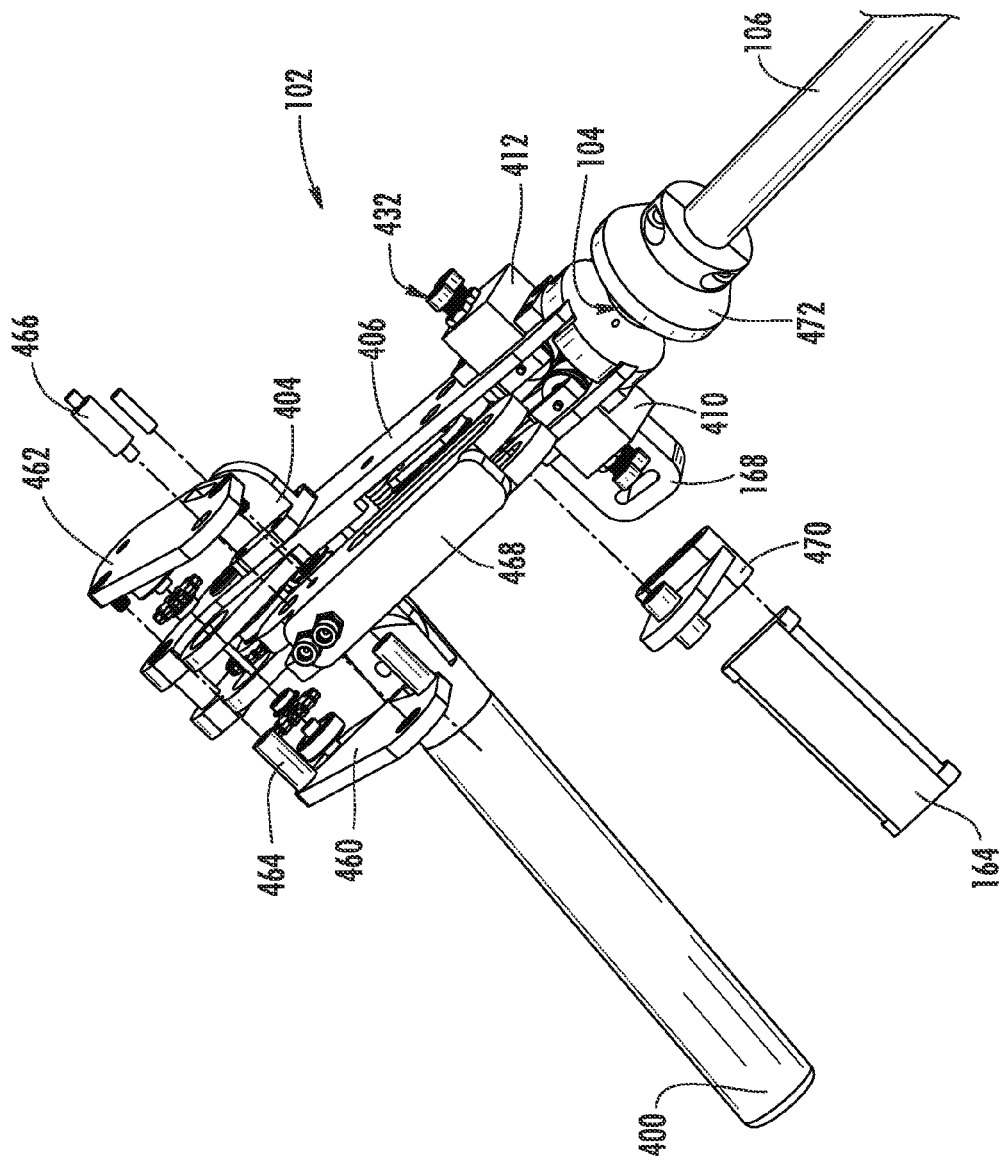
FIG. 40 is a top perspective partially exploded view of the manipulator shown in FIG. 35.
Figure 41:
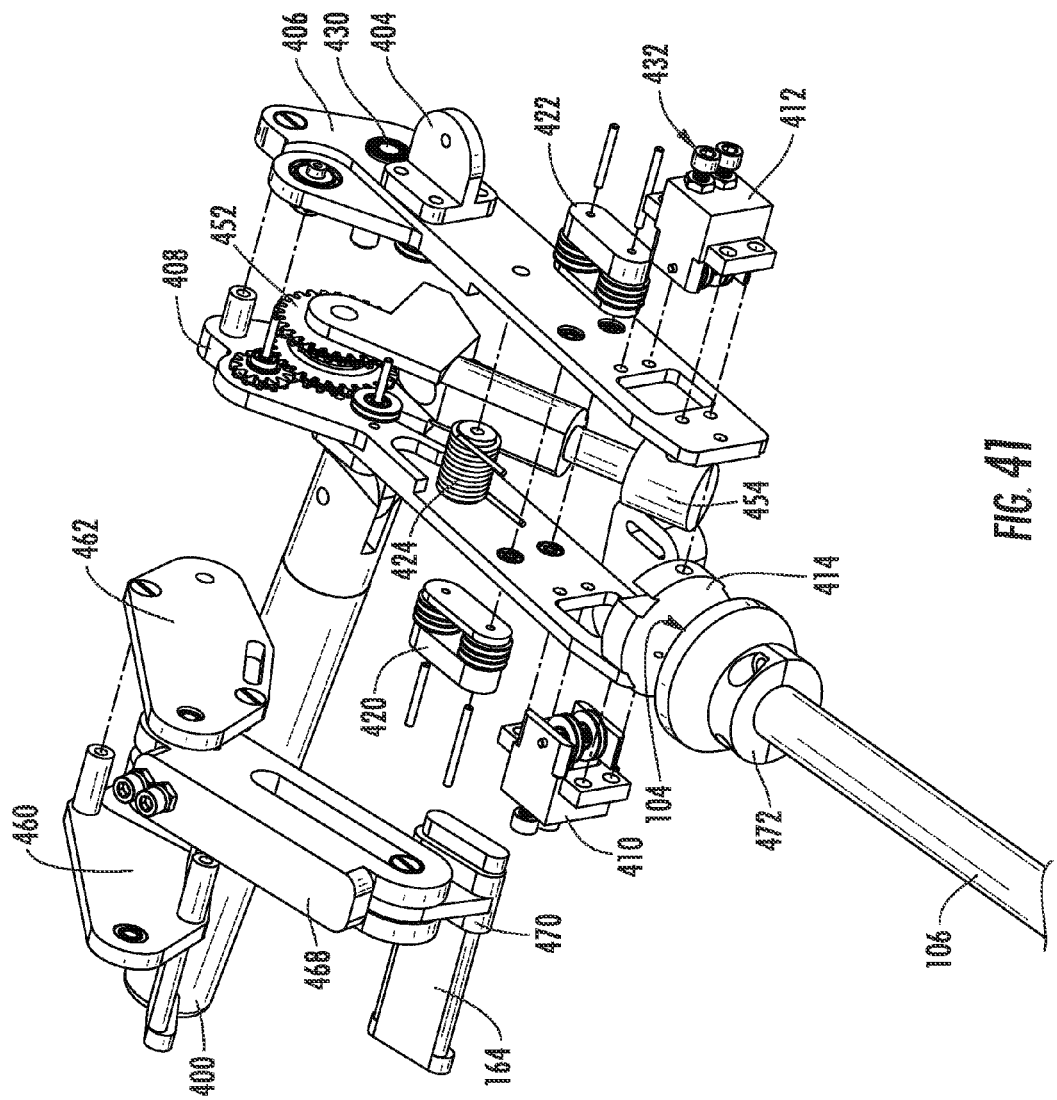
FIG. 41 is a top left perspective partially exploded view of the manipulator shown in FIG. 35.
Figure 42:
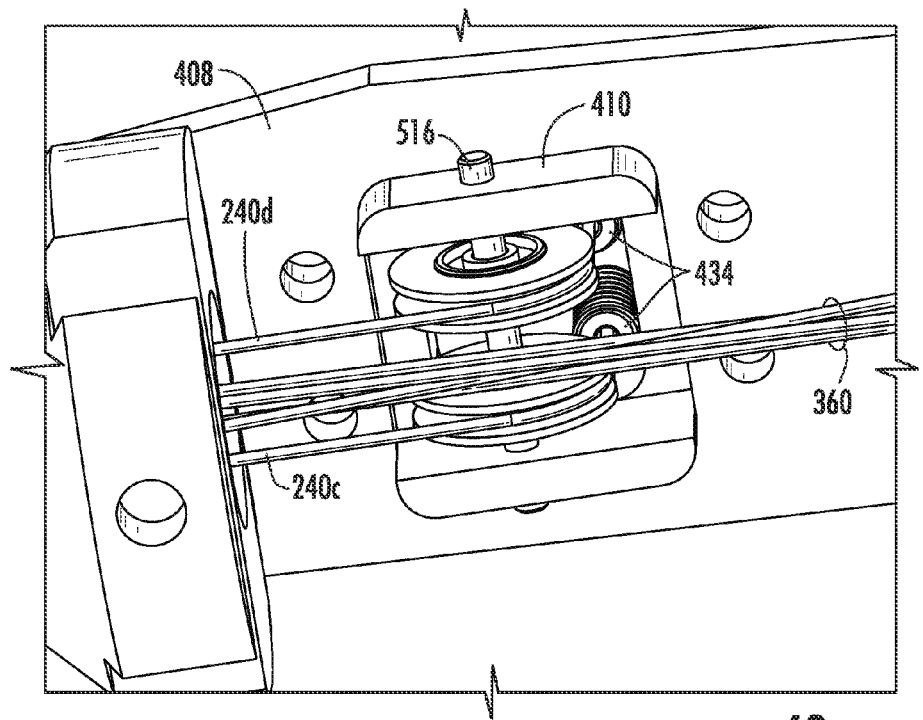
FIGS. 42-45 are perspective detail views of a universal joint tensioning assembly of the manipulator shown in FIG. 35.
Figure 43:
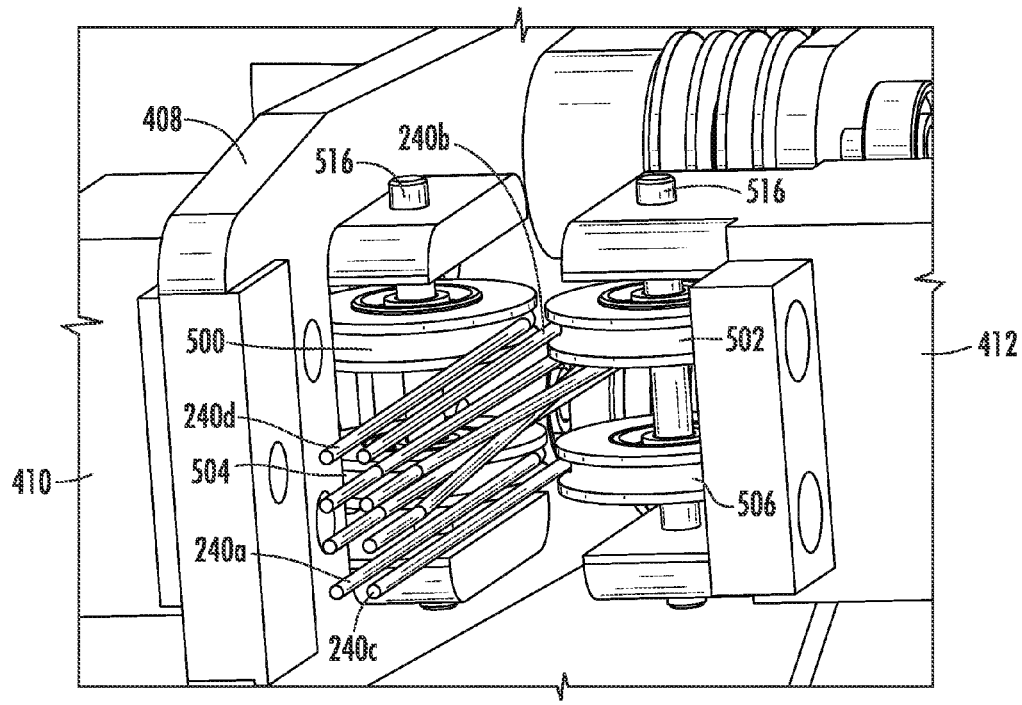

In FIGS. 40 and 41 a two-piece guard 472 is shown mounted to the tube 106. The guard 472 extends around the proximal universal joint 104. The guard 472 may be designed to limit the range of motion of the manipulator 102 and proximal universal joint 104 so that neither the proximal or distal universal joints 104, 108 can be driven beyond their operating range by the user.

FIGS. 42-45 show detail views of the universal joint static tension assemblies 410, 412. The universal joint control cables 240*a*, 240*b*, 240*c*, 240*d* tensioned by these assemblies 410, 412 pass around idling pulleys 500, 502, 504, 506 and into vented screws 434. The remainder of the cables are end effector cables, collectively designated at 360, that go by the idling pulleys 500, 502, 504, 506. In an alternate embodiment, the vented screws 434 in the tension adjustment systems 432 may be replaced by any externally threaded object that can connect to the control cables 240*a*, 240*b*, 240*c*, 240*d* that enables adjustment via the method described above for the end effector control cables 360 in the manipulator 102. The idling pulleys 500, 502, 504, 506 pivot about pins 516 such that adjustments can be made in the relative positioning of the proximal and distal universal joints 104, 108.

Figure 44:
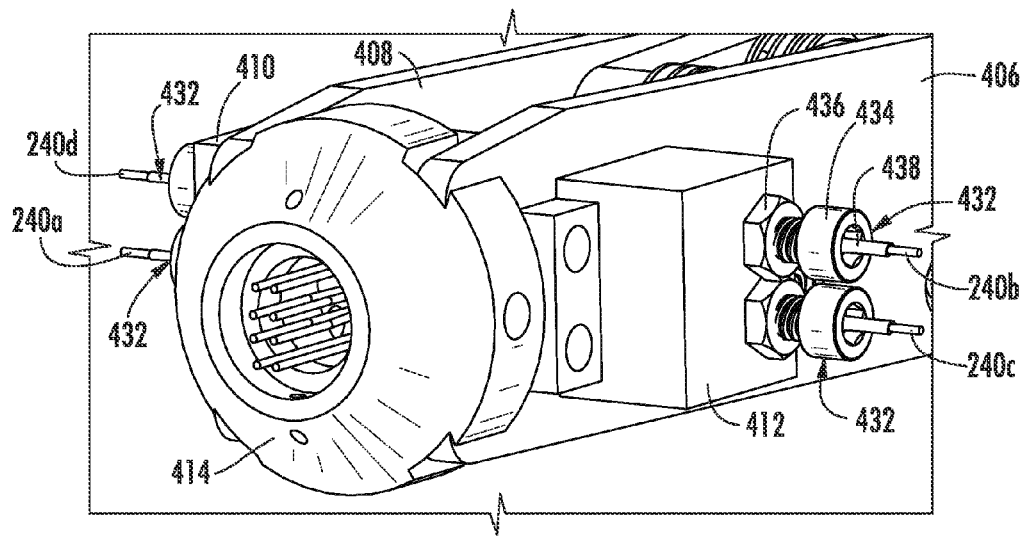
Figure 45:
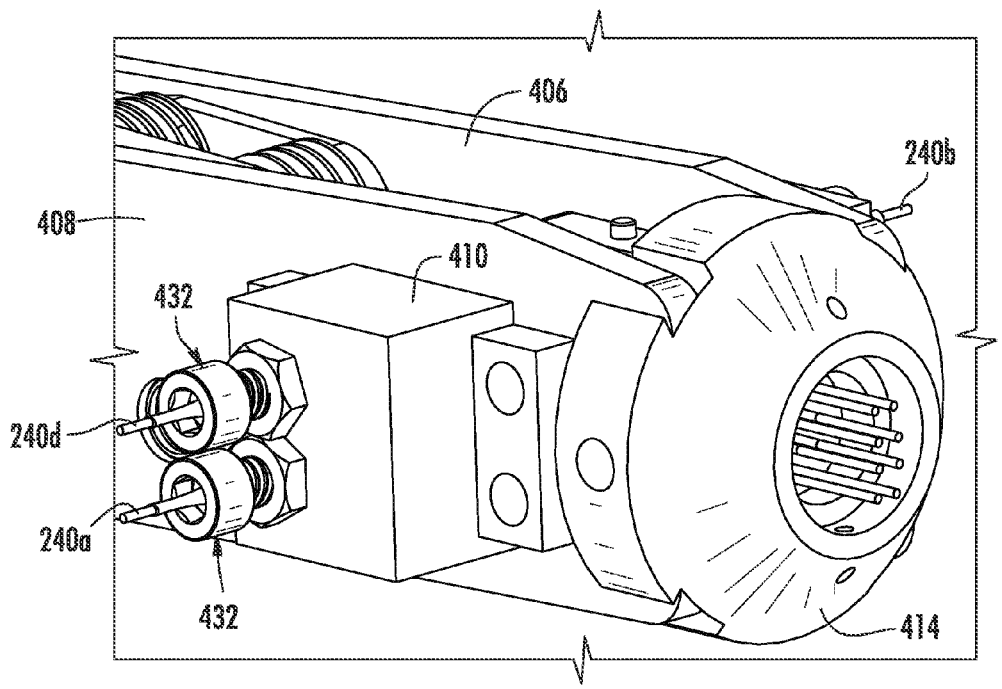

FIGS. 44 and 45 show external views of the universal joint static tension assemblies 410, 412. Tension adjustment systems 432 provide anchoring and adjustment for the universal joint control cables 240*a*, 240*b*, 240*c*, 240*d* in the same manner as the tightening and adjustment of the end effector cables 360 described above.

Figure 46:
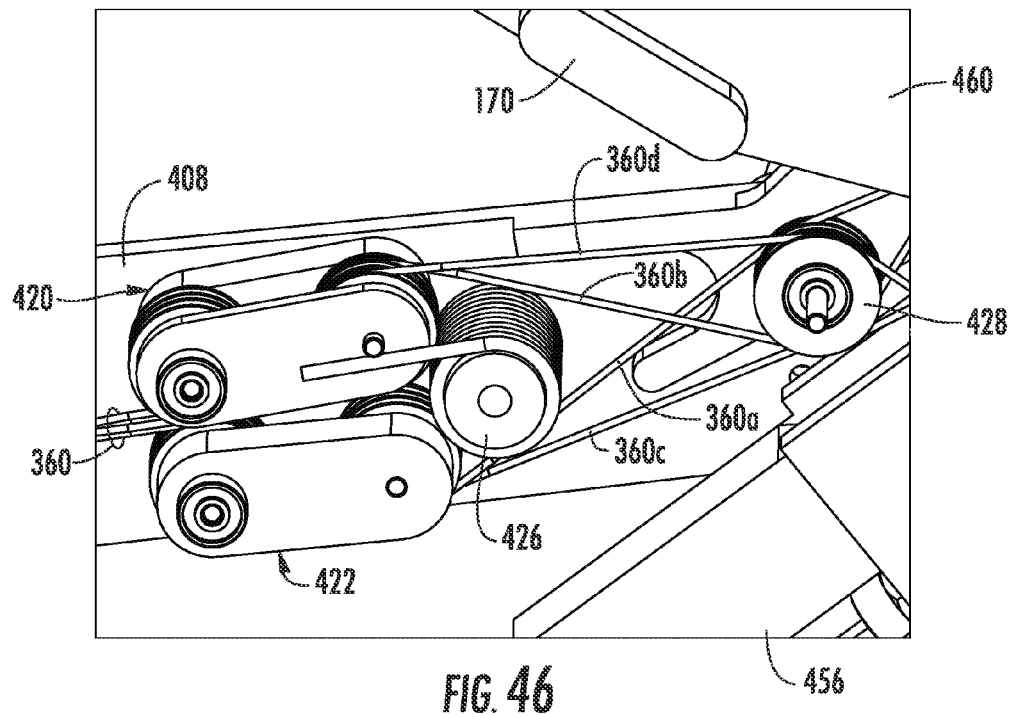
FIGS. 46-48 are perspective detail views of an active tensioning assembly for end effector control cables at the manipulator shown in FIG. 35.
Figure 47:
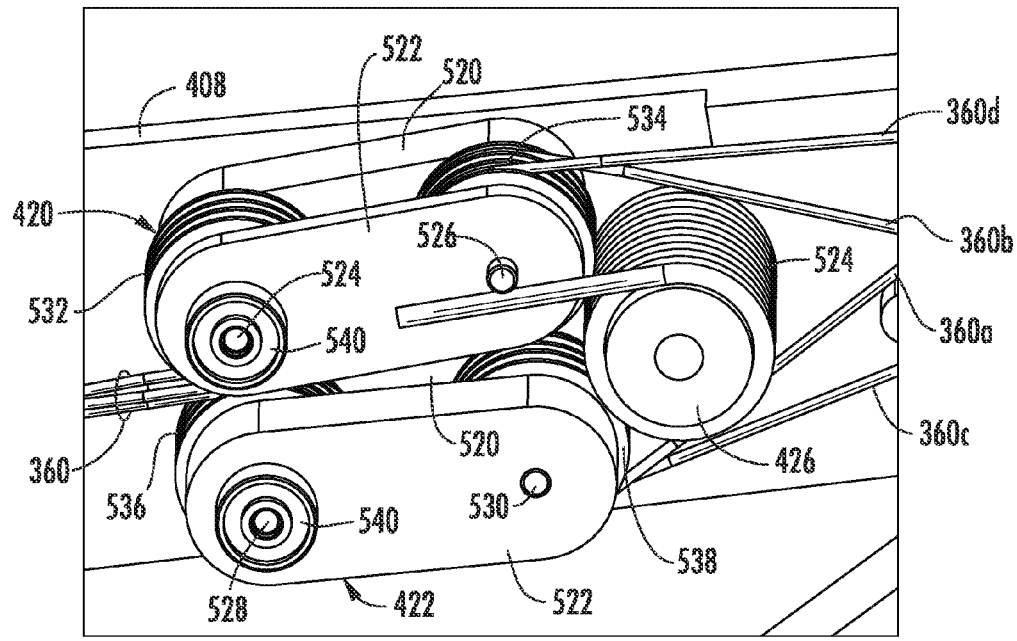
Figure 48:
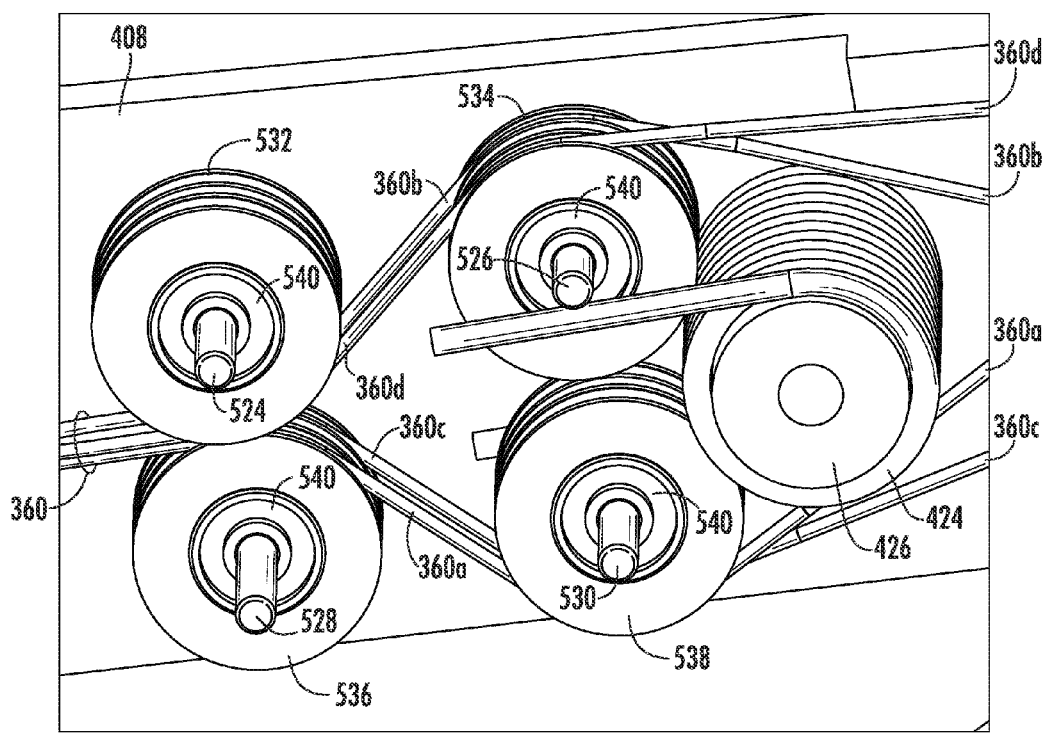

FIGS. 46, 47, and 48 show the active tensioning assemblies 420, 422, spring 424, and spacer 426 for the end effector control cables 360. The active tensioning assemblies 420, 422 each include two plates 520, 522 mounted on two pins 524, 526, 528, 530 each of which holds a pair of tensioning pulleys 532, 534, 536, 538.

The tensioning pulleys 532, 534, 536, 538 in these assemblies 420, 422 contain bearings 540 as shown in FIG. 48, and are connected to the base plates 406, 408 via the bearings 540. FIG. 48 shows the tensioning assemblies 420, 422 with plates 522 removed. The bearings 540 in these tensioning pulleys 532, 534, 536, 538 allow them to freely rotate as the control cables 360 move to transmit motion from the manipulator 102 to the end effector 110.

The cables 360*b*, 360*d* that control the proximal phalanxes 154, 156 pass under one pair of tensioning pulleys 532, over another pair of tensioning pulleys 534, and continue to a guide pulley 428. This tensioning assembly 420 can rotate on a pin 524 via a bearing 540 mounted in one of the base assembly plates 408. When the tensioning assembly 420 rotates counterclockwise, moving the second pair of tension pulleys 534 upward, the tension in cables 360*b* and 360*d* increases.

The cables 360*a*, 360*c* that control the distal phalanxes 158, 160 pass over one pair of tensioning pulleys 536, under another pair of tensioning pulleys 538, and continue to the guide pulley 428. This tensioning assembly 422 can rotate on a pin 528 via a bearing 540 mounted in one of the base assembly plates 406. When the tensioning assembly 422 rotates clockwise, moving the second pair of tension pulleys 538 downward, the tension in cables 360*a* and 360*c* increases.

The rotary spring 424, mounted on the spacer 426, applies a force to both tensioning assemblies 420, 422 via pins 526, 530 in each assembly 420, 422. This causes the tensioning assemblies 420, 422 to move apart and increase the tension in the end effector control cables 360. The motion of the universal joints 104, 108 can add or subtract tension in the end effector control cables 360, but as long as the cables 360*b*, 360*d* that control the proximal phalanxes 154, 156 maintain equal tension and the cables 360*a*, 360*c* that control the distal phalanxes 158, 160 maintain equal tension, then there will be no effect on the positioning of the end effector 110 due to motion of the universal joints 104, 108.

An alternate embodiment could include, instead of a rotary spring, a linear compression spring, linear extension spring, or flexible element acting as a spring to create the force driving the tensioning assemblies 420, 422 apart, or separate spring mechanisms.

Figure 49:
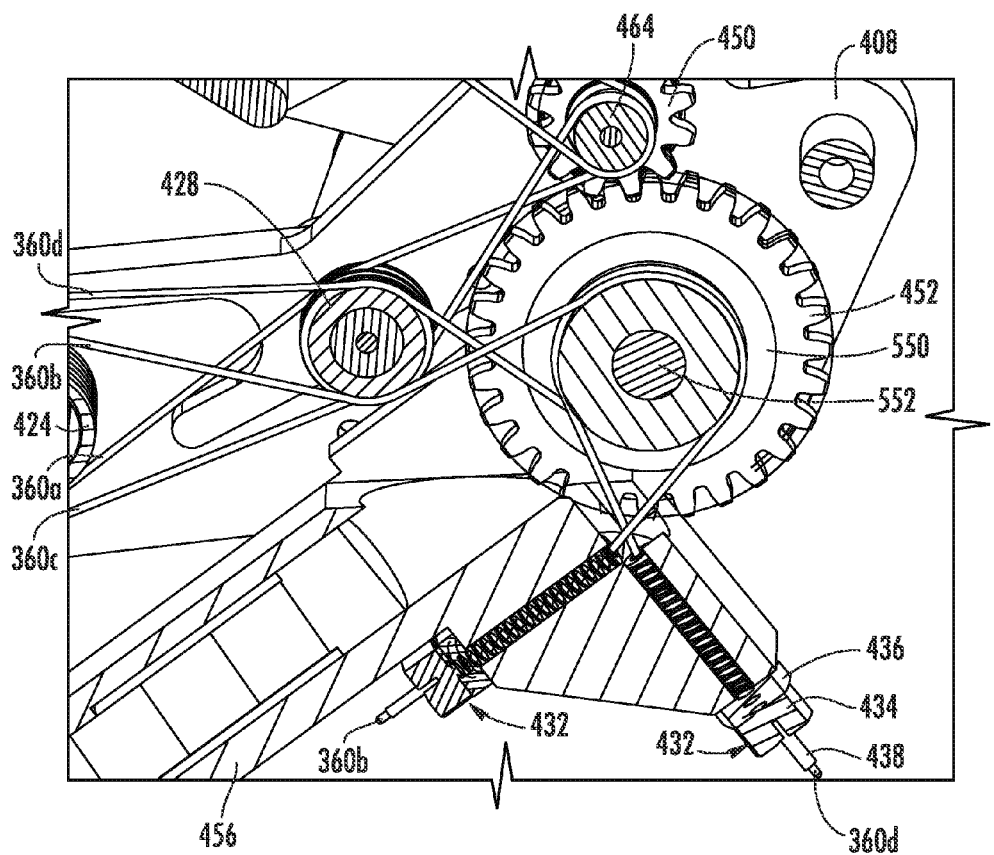
FIGS. 49 and 50 are perspective detail views of end effector cable routing at the manipulator shown in FIG. 35.

FIG. 49 shows the details of the cabling system that drives the proximal phalanxes 154, 156 of the end effector 110. After passing around a guide pulley 428, cables 360*b* and 360*d* are wrapped around a drive pulley 550 mounted on a pin 552 and enter vented screws 432 as previously discussed with respect to FIG. 39, which allows the position of the first phalanxes 154, 156 to be calibrated relative to the position of the thumb assembly 142 and primary index assembly 144 during manufacturing.

After passing around a guide pulley 428, cables 360*a* and 360*c* continue around an idler pulley 464 toward the secondary index assembly 146. As previously discussed, the primary index assembly 144 and thumb assembly 142 are coupled by a set of gears 450, 452. This allows force applied to the primary index assembly 144 to be transferred to the thumb assembly 142 to indirectly drive the cables 360*b*, 360*d* that control the proximal phalanxes 154, 156 with the thumb assembly 142.

Figure 50:
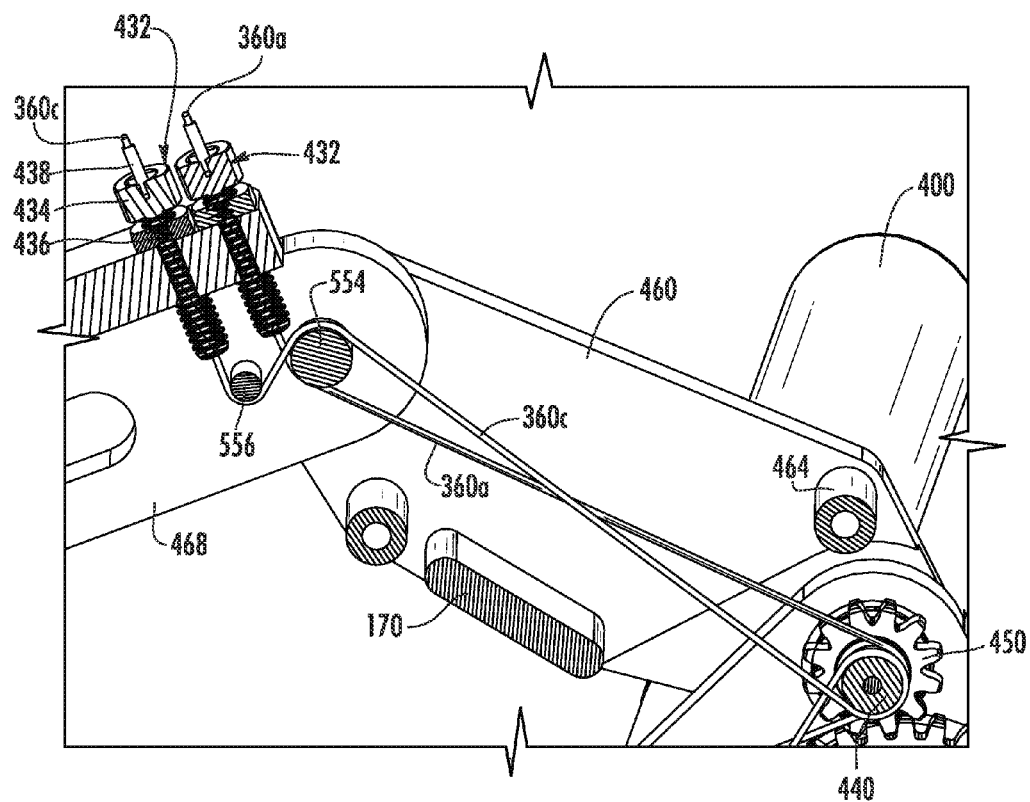

FIG. 50 shows the details of the cabling system within the manipulator 102 that controls the distal phalanxes 158, 160. After passing around an idler pulley 440, cables 360*a* and 360*c* continue to a driving pin 554 in base 468 of the secondary index assembly 142 after which they terminate in tension adjustment systems 432, as previously discussed, which may be done to calibrate the position of the secondary index assembly 146 relative to the distal phalanxes 158, 160 during manufacturing. Cable 360*c* passes around a guide pin 556 in order to be aligned with its tensioning screw 434.

If the user rotates the primary index assembly 144 and thumb assembly 142 relative to the base assembly 140 without rotating the secondary index assembly 146 relative to the primary index assembly 144, then the cables 360*a*, 360*c* that control the distal phalanxes 158, 160 will translate by the same linear distance as the cables 360*b*, 360*d* that control the proximal phalanxes 154, 156. This will result in no net motion of the controlling links 310, 312 in the end effector 110 relative to the proximal phalanxes 154, 156, and subsequently no net motion of the distal phalanxes 158, 160 relative to the proximal phalanxes 154, 156, thus imitating the motion of the manipulator 102. If the user rotates the secondary index assembly 146 relative to the primary index assembly 144 without moving the primary index assembly 144 and thumb assembly 142 relative to the base assembly 140, the cables 360*a*, 360*c* that control the distal phalanxes 158, 160 will translate while the cables 360*b*, 360*d* that control the proximal phalanxes 154, 156 will remain stationary. This will only result in motion of the distal phalanxes 158, 160 relative to the proximal phalanxes 154, 156, thus copying the motion of the user's index finger to both digits 150, 152 of the end effector 110.

The surgical instrument described herein may provide an end effector that may be articulated within the body of a patient about three axes of rotation relative to the cannula containing the instrument during use. The distal universal joint 108 provides two degrees of freedom, and a third degree of freedom arises from the instrument being rotatable within the cannula through which it is inserted. When the manipulator is rotated about its longitudinal axis, it forces a rotation of the tube section 106 within the cannula and a corresponding longitudinal rotation of the end effector, and the end effector 110 can be articulated with the three degrees of freedom, which correspond to yaw, pitch, and roll. The roll motion (rotation about the longitudinal axis) may be produced by rotating the instrument 100 as a whole, as opposed to conventional designs where an end effector is designed to rotate about its longitudinal axis independent of the rest of the instrument.

Although only a few exemplary embodiments have been shown and described in considerable detail herein, it should be understood by those skilled in the art that it is not intended to be limited to such embodiments since various modifications, omissions and additions may be made to the disclosed embodiments without materially departing from the novel teachings and advantages, particularly in light of the foregoing teachings. For example, although a manipulator with thumb and index finger actuation is shown, and an end effector with two digits each with two phalanxes are shown, the novel assembly shown and described herein may be used other types of manipulators and end effectors. Accordingly, we intend to cover all such modifications, omission, additions and equivalents as may be included within the spirit and scope as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A surgical tool for use by an operator, comprising:
 a manipulator adapted to receive at least a portion of the operator's hand, the manipulator having a longitudinal axis and a first angular position;
 a proximal universal joint having a first end and a second end, the first end of the proximal universal joint being mounted to the manipulator, the proximal universal joint including
 a center block,
 a proximal yoke at the first end of the proximal universal joint and mounted to the center block at first and second mounting locations,
 a distal yoke at the second end of the proximal universal joint and mounted to the center block at third and fourth mounting locations,
 means for pivoting the center block member about two perpendicular coplanar axes through the center block, and
 a round element at each mounting location between the center block and the proximal or distal yoke, the round elements being independent parts or integral to either of the center block or the yokes;
 a hollow elongated member having a first end, a second end, and a longitudinal axis, the first end of the elongated member being mounted to the second end of the proximal universal joint;
 a distal universal joint having a first end and a second end, the first end of the distal universal joint being mounted to the second end of the elongated member, the distal universal joint including
 a center block,
 a proximal yoke at the first end of the distal universal joint and mounted to the center block at first and second mounting locations, a distal yoke at the second end of the distal universal joint and mounted to the center block at third and fourth mounting locations, means for pivoting the center block member about two perpendicular coplanar axes through the center block, and a round element at each mounting location between the center block and the proximal or distal yoke, the round elements being independent parts or integral to either of the center block or the yokes;

cabling operatively coupling the proximal and distal universal joints, the cabling comprising four cables that each engage two of the round elements at each of the proximal and distal universal joints such that pivoting the proximal yoke of the proximal universal joint causes a corresponding motion of the distal yoke of the distal universal joint; and an end effector mounted to the second end of the distal universal joint, the end effector having a first angular position and a longitudinal axis parallel to the longitudinal axis of the manipulator, wherein at all relative positions of the manipulator and the end effector, the longitudinal axis of the manipulator and the longitudinal axis of the end effector remain parallel, and the degree of rotation of the manipulator about the longitudinal axis of the manipulator from the first angular position of the manipulator is equal to the degree of rotation of the end effector about the longitudinal axis of the end effector from the first angular position of the end effector.

2. The surgical tool of claim 1, wherein pivoting of the first end of the proximal universal joint causes the second end of the distal universal joint to move in a corresponding motion.

3. The surgical tool of claim 1, wherein the end effector comprises a base member and two opposed digits, each digit with a proximal phalange having a first end and a second end, the proximal phalange first end pivotally mounted to the base member, and a distal phalange having a first end and a second, free end, the first end pivotally mounted to the proximal phalange second end.

4. The surgical tool of claim 3, wherein the manipulator comprises a first actuator operable to concurrently control the proximal phalanxes and a second actuator operable to concurrently control the distal phalanxes.

5. The surgical tool of claim 4, wherein the second actuator is mounted to the end of at least a part of the first actuator.

6. The surgical tool of claim 5, wherein the first actuator comprises a first lever assembly adapted to be operable with the operator's thumb, wherein actuating the first lever assembly causes the proximal phalanges to move relative to each other.

7. The surgical tool of claim 6, wherein the first actuator further comprises a second lever assembly adapted to be operable with a finger of the same hand of the operator as the thumb, and wherein advancing the first and second lever assemblies toward each other causes the proximal phalanges to move toward each other.

8. The surgical tool of claim 7, wherein the second actuator comprises a third lever assembly pivotally mounted to the second lever assembly.

9. The surgical tool of claim 8, wherein each lever assembly has a longitudinal axis, and when the longitudinal axis of the third lever assembly is pivoted away from the longitudinal axis of the second lever assembly, the distal phalanges move toward each other.

10. The surgical tool of claim 9, wherein the end effector is control by four end effector control cables, and wherein two cables control the proximal phalanxes and two cables control the distal phalanges.

11. The surgical tool of claim 10, wherein the two cables that control the proximal phalanxes are operatively connected to the first lever assembly.

12. The surgical tool of claim 10, wherein the two cables that control the distal phalanxes are operatively connected to the third lever assembly.

13. The surgical tool of claim 10, wherein the end effector control cables are tensioned with resiliently biased pulleys included in the manipulator.

14. The surgical tool of claim 1, wherein the proximal and distal universal joints are controlled by universal joint control cables, and the end effector is controlled by end effector control cables, and the universal joint control cables and the end effector control cables are anchored in the manipulator and may be adjusted with means for tensioning the universal joint control cables and the end effector control.

15. A surgical tool for use by an operator, comprising:
a manipulator adapted to receive at least a portion of the operator's hand;
a proximal universal joint having a first end and a second end, the first end of the proximal universal joint being mounted to the manipulator;
a hollow elongated member having a first end, a second end, and a longitudinal axis, the first end of the elongated member being mounted to the proximal universal joint;
a distal universal joint having a first end and a second end, the first end of the distal universal joint being mounted to the second end of the elongated member; and
an end effector mounted to the second end of the distal universal joint,
wherein the proximal and distal universal joints are controlled by universal joint control cables, and the end effector is controlled by end effector control cables, and the universal joint control cables and the end effector control cables are anchored in the manipulator and may be adjusted with means for tensioning the universal joint control cables and the end effector control, and
wherein the tensioning means comprises vented screws.

16. The surgical tool of claim 15, wherein the universal joint control cables and the end effector control cables have swaged tubing at their proximal ends for abutting the vented screws when the universal joint control cables and the end effector control cables are tightened.

17. An articulation system for a surgical tool, comprising:
a proximal universal joint including a proximal end member and a distal end member, the proximal end member of the proximal universal joint having a longitudinal axis and a first angular position, each of the proximal end member and the distal end member of the proximal universal joint including
a center member for pivoting of the proximal end member and the distal end member around two substantially coplanar, perpendicular axes through the center member, and
a base portion, and opposing arms extending from the base portion, wherein each of the proximal end member and the distal end member are mounted to the center member at the arms of the base portion of the proximal end member and the distal end member, and round elements interposed between the center member and the arms at the mounting locations of the end members to the center member, the round elements being independent parts or integral to the center member or arms;

a hollow elongated member having a first end, a second end, and a longitudinal axis, the first end of the elongated member mounted to the distal end member of the proximal universal joint;

a distal universal joint including a proximal end member and a distal end member, the proximal end member of the distal universal joint mounted to the second end of the elongated member, the distal end member of the distal universal joint having a longitudinal axis and a first angular position, each of the proximal end member and the distal end member of the distal universal joint including a center member for pivoting of the proximal end member and the distal end member around two substantially coplanar, perpendicular axes through the center member, and a base portion, and opposing arms extending from the base portion, wherein each of the proximal end member and the distal end member are mounted to the center member at the arms of the base portion of the proximal end member and the distal end member, and round elements interposed between the center member and the arms at the mounting locations of the end members to the center member, the round elements being independent parts or integral to the center member or arms; and universal joint control cables engaging the round elements of the proximal universal joint and the distal universal joint for connecting the proximal universal joint and the distal universal joint such that pivoting motion of the proximal end member of the proximal universal joint relative to the longitudinal axis of the elongated member exerts force on cables to cause a corresponding pivoting motion of the distal end member of the distal universal joint, wherein at all relative positions of the proximal end member of the proximal universal joint and the distal end member of the distal universal joint the longitudinal axis of the proximal end member of the proximal universal joint and the longitudinal axis of the distal end member of the distal universal joint remain parallel, and the degree of rotation of the proximal end member of the proximal universal joint about the longitudinal axis of the proximal end member of the proximal universal joint from the first angular position of the proximal end member of the proximal universal joint is equal to the degree of rotation of the distal end member of the distal universal joint about the longitudinal axis of the distal end member of the distal universal joint from the first angular position of the distal end member of the distal universal joint.

18. The surgical tool of claim 17, wherein four universal joint control cables operatively connect the proximal and distal universal joints.

19. An articulation system for a surgical tool, comprising:
a proximal universal joint including a proximal end member and a distal end member;
a hollow elongated member having a first end, a second end, and a longitudinal axis, the first end of the elongated member first end being mounted to the distal end member of the proximal universal joint;
a distal universal joint comprising a proximal end member and a distal end member, the proximal end member of the distal universal joint being mounted to the second end of the elongated member; and universal joint control cables operatively connecting the proximal and distal universal joints, wherein pivoting motion of the proximal end member of the proximal universal joint relative to the longitudinal axis of the elongated member exerts force on cables to cause a corresponding pivoting motion of the distal end member of the distal universal joint, wherein each end member of the proximal universal joint and the distal universal joint includes a base portion and opposing arms extending from the base portion, wherein each respective proximal end member and distal end member are mounted to a center member at the arms of the proximal end member and the distal end member, and wherein the center members permit pivoting of the proximal and distal end members around two substantially coplanar, perpendicular axes through the center member, wherein the proximal universal joint and the distal universal joint each include round elements interposed between the center member and the arms at the mounting locations of the end members to the center member, and which may be independent parts or integral to the center member or arms, and wherein the round elements are engaged by the universal joint control cables, and wherein each of the four universal joint control cables engages two round elements in each universal joint.

20. A surgical tool for use by an operator, comprising:
a manipulator adapted to receive at least a portion of the operator's hand, the manipulator having a longitudinal axis and a first angular position, the manipulator comprising
a first actuator including a first lever assembly having a longitudinal axis and adapted to be operable with the operator's thumb, and a second lever assembly having a longitudinal axis and adapted to be operable with a finger of the same hand of the operator as the thumb, and
a second actuator including a third lever assembly having a longitudinal axis, and pivotally mounted to the second lever assembly, the second actuator mounted to the end of at least a part of the first actuator, a proximal universal joint having a first end and a second end, the first end of the proximal universal joint mounted to the manipulator, the proximal universal joint including
a center block, the center block pivotable around two substantially coplanar, perpendicular axes,
a proximal end member including a base portion and opposing arms extending from the base portion, the proximal end member mounted to the center block, and
a distal end member including a base portion and opposing arms extending from the base portion, the distal end member mounted to the center block, a hollow elongated member having a first end, a second end, and a longitudinal axis, the first end of the elongated member mounted to the second end of the proximal universal joint;

a distal universal joint having a first end and a second end, the first end of the distal universal joint mounted to the second end of the elongated member, the distal universal joint including
a center block, the center block pivotable around two substantially coplanar, perpendicular axes, a proximal end member including a base portion and opposing arms extending from the base portion, the proximal end member mounted to the center block, and a distal end member including a base portion and opposing arms extending from the base portion, the distal end member mounted to the center block, an end effector mounted to the second end of the distal universal joint, the end effector having a longitudinal axis parallel to the longitudinal axis of the manipulator and a first angular position, the end effector comprising a base member, and two opposed digits, each digit including a proximal phalange having a first end and a second end, the first end of the proximal phalange pivotally mounted to the base member, and a distal phalange having a first end and a second free end, the first end of the distal phalange pivotally mounted to the second end of the proximal phalange; and four control cables for controlling the end effector, two cables of the four cables controlling the proximal phalanxes and the other two cables of the four cables controlling the distal phalanges, wherein the base portions and center blocks of each of the proximal universal joint and the distal universal joint define openings for receiving the end effector control cables, wherein at all relative positions of the manipulator and the end effector, the longitudinal axis of the manipulator and the longitudinal axis of the end effector remain parallel, and the degree of rotation of the manipulator about the longitudinal axis of the manipulator from the first angular position of the manipulator is equal to the degree of rotation of the end effector about the longitudinal axis of the end effector from the first angular position of the end effector, and wherein the first actuator is operable to concurrently control the proximal phalanxes and the second actuator is operable to concurrently control the distal phalanxes such that actuating the first lever assembly causes the proximal phalanges to move relative to each other, advancing the first and second lever assemblies toward each other causes the proximal phalanges to move toward each other, and pivoting the longitudinal axis of the third lever assembly away from the longitudinal axis of the second lever assembly causes the distal phalanges to move toward each other.

* * * * *